(12) United States Patent
Young et al.

(10) Patent No.: US 6,335,183 B1
(45) Date of Patent: Jan. 1, 2002

(54) STRESS PROTEINS AND USES THEREFOR

(75) Inventors: Richard A. Young, Weston, MA (US); Douglas Young, Ruislip (GB)

(73) Assignee: Whitehead Institute for Biomedical Research, Cambridge, MA (US)

(*) Notice: Subject to any disclaimer, the term of this patent is extended or adjusted under 35 U.S.C. 154(b) by 0 days.

(21) Appl. No.: 08/461,722

(22) Filed: Jun. 5, 1995

Related U.S. Application Data

(63) Continuation of application No. 08/336,251, filed on Nov. 3, 1994, now abandoned, which is a continuation-in-part of application No. PCT/US94/06362, filed on Jun. 6, 1994, and a continuation-in-part of application No. 08/073,381, filed on Jun. 4, 1993, now abandoned, which is a continuation-in-part of application No. 07/804,632, filed on Dec. 9, 1991, now abandoned, which is a continuation of application No. 07/366,581, filed on Jun. 15, 1989, now abandoned, and a continuation-in-part of application No. PCT/US89/02619, filed on Jun. 15, 1989, which is a continuation-in-part of application No. 07/207,298, filed on Jun. 15, 1988, now abandoned.

(51) Int. Cl.[7] .......................... C12P 21/04; A61K 39/21; A61K 39/04; C12N 15/00

(52) U.S. Cl. .................... 435/69.7; 435/69.7; 435/71.1; 424/184.1; 424/188.1; 424/248.1; 530/350

(58) Field of Search .......................... 435/172.3, 69.7; 424/125.1, 184.1, 193.1, 278.1, 274.1, 194.1, 147.11, 277.1; 530/395, 404, 405, 406, 411, 350

(56) References Cited

U.S. PATENT DOCUMENTS

| | | | |
|---|---|---|---|
| 4,716,038 A | | 12/1987 | Stanford et al. ............... 424/92 |
| 4,724,144 A | * | 2/1988 | Rook et al. ................... 424/93 |
| 5,114,844 A | | 5/1992 | Cohen et al. ............... 435/7.21 |
| 5,504,005 A | * | 4/1996 | Bloom et al. ............. 435/253.1 |
| 5,580,563 A | * | 12/1996 | Tam et al. ............. 424/197.11 |

FOREIGN PATENT DOCUMENTS

| | | | |
|---|---|---|---|
| EP | 0 262 710 | 9/1987 | .......... A61K/37/02 |
| EP | 0 322 990 | 12/1988 | ............ C07K/7/06 |
| GB | 2 251 186 | 7/1992 | .......... A61K/37/02 |
| WO | WO85/05034 | 11/1985 | .......... A61K/35/74 |
| WO | WO88/00974 | 2/1988 | ........... C12N/15/00 |
| WO | WO88/05823 | 8/1988 | ........... C12N/15/00 |
| WO | WO88/06591 | 9/1988 | ........... C07H/15/12 |

(List continued on next page.)

OTHER PUBLICATIONS

Layton et al., Induction of HIV–Specific Cytotoxic T lymphocytes In Vivo with Hybrid HIV–1 V3:Ty–Virus–Like–Particles, J. Immunology, vol. 151, pp. 1097–1107, No. 2, Jul. 1993.*

More et al., Activation of cytotoxic T cells in vitro by recombinant gp96 fusion proteins irrespective of the 'fused' antigenic peptide sequence, Immunology Letters, vol. 69, pp. 275–282, 1999.*

Oettgen, H.F. and Old, L.J., "Chapter 6: The History of Cancer Immunotherapy." In *Biologic Therapy of Cancer*, De Vita, V.T., Hellman, S. and Rosenberg, S.A., eds., (London: J.B. Lippincott) pp. 98–103 (1991).

(List continued on next page.)

*Primary Examiner*—Hankyel T. Park
*Assistant Examiner*—Stacy S. Brown
(74) *Attorney, Agent, or Firm*—Hamilton, Brook, Smith & Reynolds, P.C.

(57) ABSTRACT

The present invention relates to stress proteins and methods of modulating an individual's immune response. In particular, it relates to the use of such stress proteins in immune therapy and prophylaxis, which results in an induction or enhancement of an individual's immune response and as an immunotherapeutic agent which results in a decrease of an individual's immune response to his or her own cells. The present invention also relates to compositions comprising a stress protein joined to another component, such as a fusion protein in which a stress protein is fused to an antigen. Further, the present invention relates to a method of generating antibodies to a substance using a conjugate comprised of a stress protein joined to the substance.

36 Claims, 10 Drawing Sheets

FOREIGN PATENT DOCUMENTS

| WO | WO89/12455 | 12/1989 | |
|----|------------|---------|---|
| WO | WO90/15873 | 12/1990 | |
| WO | WO91/02542 | 3/1991 | .......... A61K/39/04 |
| WO | WO91/15572 | 10/1991 | ............ C12N/1/20 |
| WO | WO92/08484 | 5/1992 | .......... A61K/39/04 |
| WO | WO92/08488 | 5/1992 | .......... A61K/39/39 |
| WO | WO93/17712 | 9/1993 | |
| WO | WO94/03208 | 2/1994 | |
| WO | 98/35705 | 2/1998 | |

OTHER PUBLICATIONS

Hudson, C.N., et al., "Active Specific Immunotherapy for Ovarian Cancer," *The Lancet,* 2:877–879 (Oct. 23, 1976).

Sparks, F.C., et al., "Immunology and Adjuvant Chemoimmunotherapy of Breast Cancer," *Arch Surg,* 111:1057–1062 (Oct. 1976).

Voellmy, et al.: Isolation and functional analysis . . . : P.N.A.C.: vol. 82: pp. 4949–4953, 1985.

Arnosti, et al. : Characterization of Heat Shock . . . : J. Bact.: vol. 168, No. 3: pp. 1243–1249, Dec. 1986.

Gomes, et al.: Heat Shock Protein . . . : J. Bact.: vol. 168, No. 3: pp. 923–930, Nov. 1986.

Lussow, et al.: Mycobacterial heat–shocked proteins as carrier molecules: Eur. J. Immunol.: vol. 21: pp. 2297–2302, 1991.

Barrios, et al.: Mycobacterial heat–shocked proteins as carrier molecules . . . :Eur. J. Immunol. : vol. 22 : pp. 1365–1372, 1992.

Lamb, J.R., et al., "Stress Proteins may Provide a Link Between the Immune Response to Infection and Autoimmunity", *Int'l. Immun.,* 1(2):191–196 (1989).

Young, R. A., "Stress Proteins and Immunology," *Annu. Rev. Immunol.,* 8:401–420 (1990).

Lussow, A. R., et al., "Mycobacterial heat–shock proteins as carrier molecules," *Eur. J. Immunol.,* 21:2297–2302 (1991).

Barrios, C. et al., "Mycobacterial heat–shock proteins as carrier molecules. II: The use of the 70–kDa mycobacterial heat–shock protein as carrier for conjugated vaccines can circumvent the need for adjuvants and *Bacillus Calmette Guerin* priming," *Eur. J. Immunol.,* 22:1365–1372 (1992).*

Blander, S. J. and Horwitz, M. A., "Major Cytoplasmic Membrane Protein of *Legionella pneumophila,* a Genus Common Antigen and Member of the hsp 60 Family of Heat Shock Proteins, Induces Protective Immunity in a Guinea Pig Model of Legionnaires' Disease," *J. Clin. Invest.,* 91:717–723 (1993).*

Giudice, G. D., et al., "Priming to Heat Shock Proteins in Infants Vaccinated against Pertussis," *J. Immunol.,* 150(5):2025–2032 (1993).*

Agranovsky, A. A., et al., "Putative 65 kDa Protein of Beet Yellows Closterovirus Is a Homologue of HSP70 Heat Shock Proteins," *J. Mol. Biol.,* 217:603–610 (1991).*

Miller, A. et al., "Immunotherapy in autoimmune diseases," *Curr. Opinion in Immun.,* 3:936–940 (1991).*

Nadler, S. G. et al., "Interaction of the Immunosupressant Deoxyspergualin with a Member of the Hsp70 Family of Heat Shock Proteins," *Science,* 258:484–486 (1992).*

Elias, D. et al., "Induction and therapy of autoimmune diabetes in the non–obese diabetic (NOD/Lt) mouse by a 65–kDa heat shock protein," *Proc. Natl. Acad. Sci. USA,* 87:1576–1580 (1990).*

Thole, J. E.R. et al., "Characterization, Sequence Determination, and Immunogenicity of a 64–Kilodalton Protein of *Mycobacterium bovis* BCG Expressed in *Escherichia coli* K–12," *Infection & Immunol.,* 55(6):1466–1475 (1987).*

Young, R. A. et al., "Genes for the major protein antigens of the leprosy parasite *mycobacterium leprae,*" *Nature,* 316:450–452 (1985).*

Husson, R. N. and Young, R.A., "Genes for the major protein antigens of *Mycobacterium tuberculosis:* The etiologic agents of tuberculosis and leprosy share an immunodominant antigen," *Proc. Natl. Acad. Sci. USA,* 84:1679–1683 (1987).*

Young, D. et al., "Stress proteins are immune targets in leprosy and tuberculosis," *Proc. Natl. Acad. Sci. USA,* 85:4267–4270 (1988).*

Lindquist, S. and Craig, E. A., "The Heat–Shock Proteins," *Annu. Rev. Genet.,* 22:631–677 (1988).*

Welch, W. J. et al., "Biochemical Characterization of the Mammalian Stress Proteins and Identification of Two Stress Proteins as Glucose– and $CA^{2+}$–Ionophore–regulated Proteins," *J. Biol. Chem.,* 258(11):7102–7111 (1983).*

Ardeshir, et al., "A 75 Kd Merozoite Surface Protein of *Plasmodium Falciparum* which is Related to the 70 kd Heat–Shcok Proteins", *EMBO J.,* 6(2):493–499 (1987).*

Vodkin, M.H. and Williams, J.C., "A Heat Shock Operon in *Coxiella burnetii* Produces a Major Antigen Homologous to a Protein in Both Mycobacteria and *Escherichia coli*", *J. of Bacteriology,* 170(3):1227–1234 (1988).*

Thole, J.E.R., et al., "Antigenic relatedness of a strongly immunogenic 65 kDA mycobacterial protein antigen with a similarly sized ubiquitous bacterial common antigen", *Microbial Pathogenesis,* 4:71–83 (1988).* van Eden, W., et al., "Cloning of the mycobacterial epitope recognized by T lymphocytes in adjuvant arthritis", *Nature,* 331(14):171–173 (1988).*

Del Guidice, G., et al., "Heat shock proteins as "super"–carriers for sporozoite peptide vaccines?", *Research in Immunol.,* 162:703–707 (1991).*

Young, D.B., et al., "The 65kDa antigen of mycobacteria—a common bacterial protein?", *Immunol. Today,* 8(7–8):215–219 (1987).

Shinnick, T.M., et al., "The Etiologic Agents of Leprosy and Tuberculosis Share an Immunoreactive protein Antigen with the Vaccine Strain *Mycobacterium bovis* BCG", *Infect. and Immun.,* 55(8):1932–1935 (1987).

Kaufmann, S.H.E., et al., "Enumeration of T cells reactive with *Mycobacterium tuberculosis* organisms and specific for the recombinant mycobacterial 64–kDa protein", *Eur. J. Immunol.,* 17:351–357 (1987).

Arrigo, A. and Welch, W.J., "Characterization and Purification of the Small 28,000–Dalton Mammalian Heat Shock Protein", *J. Biol. Chem.,* 262(32):15359–15369 (1987).

Catelli, M.G., et al., "The common 90–kd protein component of non–transformed '8S' steroid receptors is a heat–shock protein", *EMBO J.,* 4(12):3131–3135 (1985).

Welch, W.J. and Feramisco, J.R., "Rapid Purification of Mammalian 70,000–Dalton Stress Proteins: Affinity of the Proteins for Nucleotides", *Mol. Cell. Biol.,* 5(6):1229–1237 (1985).

Welch, W.J. and Feramisco, J.R., "Purification of the Major Mammalian Heat Shock Proteins", *J. Biol. Chem.,* 257(24):14949–14959 (1982).

Zylicz, M., et al., "The grpE Protein of *Escherichia coli*", *J. Biol. Chem.*, 262(36):17437–17442 (1987).

Chandrasekhar, G.N., et al., "Purification and Properties of the groES Morphogenetic Protein of *Escherichia coli*", *J. Biol. Chem.*, 261(26):12414–12419 (1986).

Zylicz, M. and Georgopoulos, C., "Purification and Properties of the *Escherichia coli* dnaK Replication Protein", *J. Biol. Chem.*, 259(14):8820–8825 (1984).

* cited by examiner

```
      1,         10,         20,         30,         40,         50,         60,         70,
HUMP1  MLRLPTVFRQMRPVSRVLAPHLTRAYAKDVKFGADARALMLQGVDLLADAVAVTMGPKGRTVIIEQSWGS
                                 ::  :::::  ::  :::::::  ::::: ::::::
GROEL  ------------------------------MA-------AKDVKFGNDARVKMLRGVNVLADAVKVTLGPKGRNVVLDKSFGA 71,        80,         90,        100,        110,        120,        130,        140,
HUMP1  PKVTKDGVTVAKSIDLKDKYKNIGAKLVQDVANNTNEEAGDGTTTATVLARSIAKEGFEKISKGANPVEI
       ::   ::: ::  ::: ::     :  :           :::::::::  ::    ::
GROEL  PTITKDGVSVAREIEPEDKFENMGAQMVKEVASKANDAAGDGTTTATVLAQAIITEGLKAVAAGMNPMDL 141,       150,        160,        170,        180,        190,        200,        210,
HUMP1  RRGVMLAVDAVIAELKKQSKPVTTPEEIAQVATISANGDKEIGNIISDAMKKVGRKGVITVKDGKTLNDE
       :::   :::::  :  :: : ::::: ::::: ::::  :::::::::: :: :::::::::::::::
GROEL  KRGIDKAVTAAVEELKALSVPCSDSKAIAQVGTISANSDETVGKLIAEAMDKVGKEGVITVEDGTGLQDE 211,       220,        230,        240,        250,        260,        270,        280,
HUMP1  LEIIEGMKFDRGYISPYFINTSKGQKCEFQDAYVLLSEKKISSIQSIVPALEIANAHRKPLVIIAEDVDG
       ::: ::: :::::::::::  :   ::  ::::::::  :     :::  :: :   ::::::::::::
GROEL  LDVVEGMQFDRGYLSPYFINKPETGAVELESPFILLADKKISNIREMLPVLEAVAKAGKPLLIIAEDVEG 281,       290,        300,        310,        320,        330,        340,        350,
HUMP1  EALSTLVLNRLKVGLQVVAVKAPGFGDNRKNQLKDMAIATGGAVFGEEGLTLNLEDVQPHDLGKVGEVIV
       ::: : ::::::::: :::::::::::::::: :: ::::::::::::    :  :::::::::::::
GROEL  EALATAVVNTIRGIVKVAAVKAPGFGDRRKAMLQDIATLTGGTVISEE-IGMELEKATLEDLGQAKRVVI 351,       360,        370,        380,        390,        400,        410,        420,
HUMP1  TKDDAMLLKGKGDKAQIEKRIQEIIEQLDVTTSEYEKEKLNERLAKLSDGVAVLKVGGTSDVEVNEKKDR
       ::    :::::  ::::::: : ::  ::        ::::: :::: :::::: ::  :    :::::
GROEL  NKDTTTIIDGVGEEAAIQGRVAQIRQQIEEATSDYDREKLQERVAKLAGGVAVIKVGAATEVEMKEKKAR
```

Figure 2A

```
         421,        430,        440,        450,        460,        470,        480,        490,
HUMP1    VTDALNATRAAVEEGIVLGGGCALLRCIPALDSLTPANEDQKIGIEIIKRTLKIPAMTIAKNAGVEGSLI
         ::  ::::::::::  ::  ::: :  :     : :::: ::    ::  :  ::       ::
GROEL    VEDALHATRAAVEEGVVAGGGVALIRVASKLADLRGQNEDQNVVSSSL-RAMEAPLRQIVLNCGEEPSVV 491,        500,        510,        520,        530,        540,        550,        560,
HUMP1    VEKIMQSSEVGYDAMAGDFVNMVEKGIIDPTKVVRTALLDAAGVASLLTTAEVVVTEIPKEEKDPGMGA
         ::  :      :      :: :::::::: :::::::  ::::    ::    ::    ::   ::
GROEL    ANTVKGGDGNYGYNAATEEYGNMIDMGILDPTKVTRSALQYAASVAGLMITTECMVTDLPKND-AADLGA 561,        570,
HUMP1    MGGMGG---GMGGGMF
         ::::: :::::  :
GROEL    AGGMGGMGGMGGMM-

Total score = 4667,  5 breaks
  276 identities out of 545 possible matches between residues 25 random runs
Alignment score =  65.34  SD  Standard deviation =  18.94   Mean = 3429.48
```

Figure 2B

```
        1,          10,         20,         30,         40,         50,         60,         70,
HUMP1   MLRLPTVFRQMRPVSRVLAPHLTRAYAKDVKFGADARALMLQGVDLLADAVAVTMGPKGRTVIIEQSWGS
        ::                                  :::::  ::  :::::::::::::::::::::::
ML65K   M------------------------------AKTIAYDEEARRGLERGLNSLADAVKVTLGPKGRNVVLEKKWGA 71,         80,         90,         100,        110,        120,        130,        140,
HUMP1   PKVTKDGVTVAKSIDLKDKYKNIGAKLVQDVANNTNEEAGDGTTTATVLARSIAKEGFEKISKGANPVEI
        ::  :::  :::  :: ::  :::::::::: :  :::::::::::::::: :: :::::::  :
ML65K   PTITNDGVSIAKEIELEDPYEKIGAELVKEVAKKTDDVAGDGTTTATVLAQALVKEGLRNVAAGANPLGL 141,        150,        160,        170,        180,        190,        200,        210,
HUMP1   RRGVMLAVDAVIAELKKQSKPVTTPEEIAQVATISANGDKEIGNIISDAMKKVGRKGVITVKDGKTLNDE
        :: ::  :::  :::::::  ::  ::::::::::  ::::  :::::::::::::::::::::::
ML65K   KRGIEKAVDKVTETLLKDAKEVETKEQIAATAAISA-GDQSIGDLIAEAMDKVGNEGVITVEESNTFGLQ 211,        220,        230,        240,        250,        260,        270,        280,
HUMP1   LEIIEGMKFDRGYISPYFINTSKGQKCEFQDAYVLLSEKKISSIQSIVPALEIANAHRKPLVIIAEDVDG
        ::::::::::::::::::::: :::    :::::::::::::: :::: :: :::  ::::::::::::
ML65K   LELTEGMRFDKGYISGYFVTDAERQEAVLEEPYILLVSSKVSTVKDLLPLLEKVIQAGKSLLIIAEDVEG 281,        290,        300,        310,        320,        330,        340,        350,
HUMP1   EALSTLVLNRLKVGLQVVAVKAPGFGDNRKNQLKDMAIATGGAVFGEEGLTLNLEDVQPHDLGKVGEVIV
        ::::::: ::::::::::: ::::::::::  ::::::::::: :::::::::::   :::  :
ML65K   EALSTLVVNKIRGTFKSVAVKAPGFGDRRKAMLQDMAILTGAQVISEE-VGLTLENTDLSLLGKARKVVM 351,        360,        370,        380,        390,        400,        410,        420,
HUMP1   TKDDAMLLKGKGDKAQIEKRIQEIIEQLDVTTSEYEKEKLNERLAKLSDGVAVLKVGGTSDVEVNEKKDR
        :::  :::::: ::  :::  ::  :::::  ::: :::::::::::::::::  :: :::  :::::
ML65K   TKDETTIVEGAGDTDAIAGRVAQIRTEIENSDSDYDREKLQERLAKLAGGVAVIKAGAATEVELKERKHR
```

Figure 3A

```
              421,      430,       440,       450,       460,       470,       480,       490,
HUMP1         VTDALNATRAAVEEGIVLGGGCALLRCIPALDSLTPANEDQKIGIEIIKRTLKIPAMTIAKNAGVEGSLI
                ::  :::::::  ::          ::::            ::   ::  ::       ::  :: :
ML65K         IEDAVRNAKAAVEEGIVAGGGVTLLQAAPALDKLKLTGDEAT-GANIVKVALEAPLKQIAFNSGMEPGVV 491,      500,       510,       520,       530,       540,       550,       560,
HUMP1         VEKIMQSSSEVGYDAMAGDFVNMVEKGIIDPTKVVRTALLDAAGVASLLTTAEVVVTEIPKEEKDPGMGA
                ::       :::  ::  ::  ::    ::::  ::::: :::  :::::: ::::  :  :::
ML65K         AEKVRNLSVGHGLNAATGEYEDLLKAGVADPVKVTRSALQNAASIAGLFTT-EAVVADKPEKTAAPASDP 561,       570,
HUMP1         MGGMGGGMGGGGMF
              ::::: ::   :
ML65K         TGGMGG-MD---F

Total score = 4552, 7 breaks
  255 identities out of 540 possible matches between residues 25 random runs
Alignment score = 47.73 SD    Standard deviation = 23.86    Mean = 3413.16
```

Figure 3B

```
              10         20         30         40         50         60         70
       ,         ,         ,         ,         ,         ,         ,
HUMP1  MLRLPTVFRQMRPVSRVLAPHLTRAYAKDVKFGADARALMLQGVDLLADAVATMGPKGRTVIIEQSWGS
         ::                            ::     :: ::::: :::    :: :: ::
TB65K  M------------------------AKTIAYDEEAARRGLERGLNALADAVKVTLGPKGRNVLEKKWGA 80         90        100        110        120        130        140
       ,         ,         ,         ,         ,         ,         ,
HUMP1  PKVTKDGVTVAKSIDLKDKYKNIGAKLVQDVANNTNEEAGDGTTTATVLARSIAKEGFEKISKGANPVEI
         :  :::    :::::   ::: :::: :::  : ::::::::::::::: ::: :::::::::::
TB65K  PTITNDGVSIAKEIELEDPYEKIGAELVKEVAKKTDDVAGDGTTTATVLAQALRKEGLRNVAAGANPLGL 150        160        170        180        190        200        210
       ,         ,         ,         ,         ,         ,         ,
HUMP1  RRGVMLAVDAVIAELKKQSKPVTTPEEIAQVATISANGDKEIGNIISDAMKKVGRKGVITVKDGKTLNDE
         :  :::::::: :: :::   :::: :  :: :::   :::   ::::: ::::: :::::: :::
TB65K  KRGIEKAVEKVTETLLKGAKEVETKEQIAATAAISA-GDQSIGDLIAEAMDKVGNEGVITVEESNTFGLQ 220        230        240        250        260        270        280
       ,         ,         ,         ,         ,         ,         ,
HUMP1  LEIIEGMKFDRGYISPYFINTSKGQKCEFQDAYVLLSEKKISSIQSIVPALEIANAHRKPLVIIAEDVDG
       :: ::: ::::::::::    ::  ::   ::: ::::  :::    ::  ::: ::::::::::::
TB65K  LELTEGMRFDKGYISGYFVTDPERQEAVLEDPYILLVSSKVSTVKDLLPLLEKVIGAGKPLLIIAEDVEG 290        300        310        320        330        340        350
       ,         ,         ,         ,         ,         ,         ,
HUMP1  EALSTLVLNRLKVGLQVVAVKAPGFGDNRKNQLKDMAIATGGAVFGEEGLTLNLEDVQPHDLGKVGEVIV
       :::::::: :::::::::::::::::::   :::::: ::::: :::::::::::    :::: ::::
TB65K  EALSTLVVNKIRGTFKSVAVKAPGFGDRRKAMLQDMAILTGGQVISEE-VGLTLENADLSLLGKARKVVV 360        370        380        390        400        410        420
       ,         ,         ,         ,         ,         ,         ,
HUMP1  TKDDAMLLKGKGDKAQIEKRIQEIIEQLDVTTSEYEKEKLNERLAKLSDGVAVLKVGGTSDVEVNEKKDR
       :::  :::   ::: ::  ::::::::::: ::    :: :::: ::::::::  ::::  ::::::::
TB65K  TKDETTIVEGAGDTDAIAGRVAQIRQEIENSDSDYDREKLQERLAKLAGGVAVIKAGAATEVELKERKHR
```

Figure 4A

```
         421,         430,        440,         450,         460,         470,         480,         490,
HUMP1    VTDALNATRAAVEEGIVLGGGCALLRCIPALDSLTPANEDQKIGIEIIKRTLKIPAMTIAKNAGVEGSLI
         ::  ::::::: :::    ::  :  ::         :    ::  : :::::       : ::  :: :
TB65K    IEDAVRNAKAAVEEGIVAGGGVTLLQAAPTLDELK-LEGDEATGANIVKVALEAPLKQIAFNSGLEPGVV 491,         500,        510,         520,         530,         540,         550,         560,
HUMP1    VEKIMQSSEVGYDAMAGDFVNMVEKGIIDPTKVVRTALLDAAGVASLLTTAEVVVTEIPKEEKDPGMGA
          :    ::  :    ::      ::  :  :: :::::  ::: :  :::   ::     ::::
TB65K    AEKVRNLPAGHGLNAQTGVYEDLLAAGVADPVKVTRSALQNAASIAGLFLTTEAVVADKPEKEKASVPG- 561,         570,
HUMP1    MGGMGGGMGGGMF
         ::   :::  ::
TB65K    ----GGDMGGGMDF

Total score = 4560, 5 breaks
  257 identities out of 540 possible matches between residues 25 random runs
Alignment score = 49.36    SD    Standard deviation =  23.23    Mean = 3413.16
```

Figure 4B

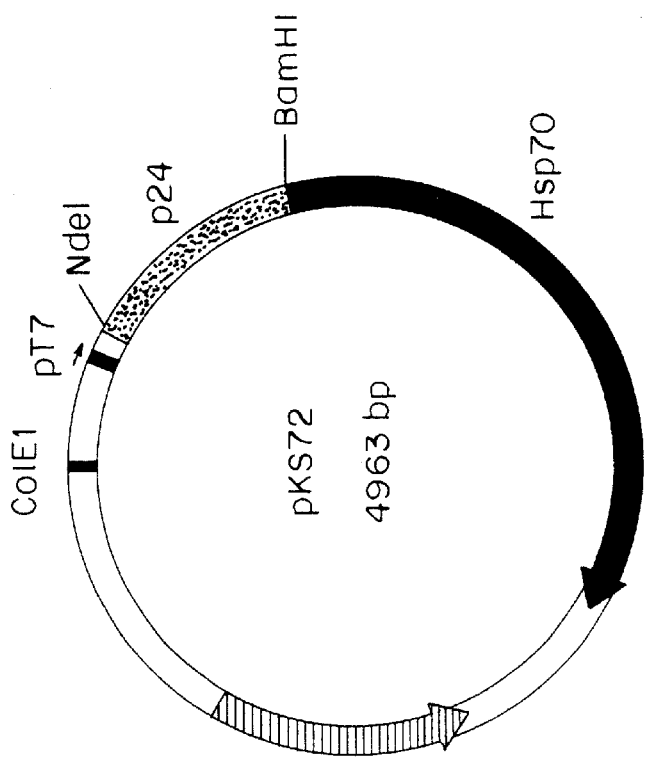
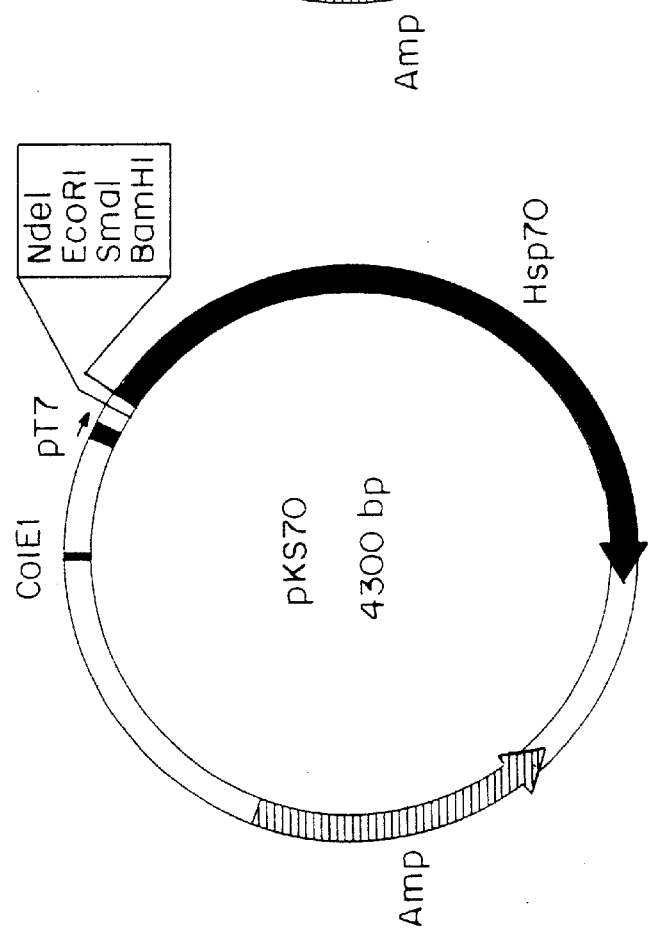
FIG. 6

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 573 amino acids
      (B) TYPE: amino acid
      (D) TOPOLOGY: linear (ii) MOLECULE TYPE: protein (xi) SEQUENCE DESCRIPTION: SEQ ID NO:1:

```
Met Leu Arg Leu Pro Thr Val Phe Arg Gln Met Arg Pro Val Ser Arg
1               5                   10                  15

Val Leu Ala Pro His Leu Thr Arg Ala Tyr Ala Lys Asp Val Lys Phe
            20                  25                  30

Gly Ala Asp Ala Arg Ala Leu Met Leu Gln Gly Val Asp Leu Leu Ala
        35                  40                  45

Asp Ala Val Ala Val Thr Met Gly Pro Lys Gly Arg Thr Val Ile Ile
    50                  55                  60

Glu Gln Ser Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ala Gly Asp Gly
            100                 105                 110

Thr Thr Thr Ala Thr Val Leu Ala Arg Ser Ile Ala Lys Glu Gly Phe
        115                 120                 125

Glu Lys Ile Ser Lys Gly Ala Asn Pro Val Glu Ile Arg Arg Gly Val
    130                 135                 140

Met Leu Ala Val Asp Ala Val Ile Ala Glu Leu Lys Lys Gln Ser Lys
```

```
            145                 150                 155                 160
Pro Val Thr Thr Pro Glu Glu Ile Ala Gln Val Ala Thr Ile Ser Ala
                165                 170                 175

Asn Gly Asp Lys Glu Ile Gly Asn Ile Ile Ser Asp Ala Met Lys Lys
            180                 185                 190

Val Gly Arg Lys Gly Val Ile Thr Val Lys Asp Gly Lys Thr Leu Asn
            195                 200                 205

Asp Glu Leu Glu Ile Ile Glu Gly Met Lys Phe Asp Arg Gly Tyr Ile
            210                 215                 220

Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Ile Gln Ser
                245                 250                 255

Ile Val Pro Ala Leu Glu Ile Ala Asn Ala His Arg Lys Pro Leu Val
                260                 265                 270

Ile Ile Ala Glu Asp Val Asp Gly Glu Ala Leu Ser Thr Leu Val Leu
            275                 280                 285

Asn Arg Leu Lys Val Gly Leu Gln Val Val Ala Val Lys Ala Pro Gly
290                 295                 300

Phe Gly Asp Asn Arg Lys Asn Gln Leu Lys Asp Met Ala Ile Ala Thr
305                 310                 315                 320

Gly Gly Ala Val Phe Gly Glu Glu Gly Leu Thr Leu Asn Leu Glu Asp
                325                 330                 335

Val Gln Pro His Asp Leu Gly Lys Val Gly Glu Val Ile Val Thr Lys
            340                 345                 350

Asp Asp Ala Met Leu Leu Lys Gly Lys Gly Asp Lys Ala Gln Ile Glu
            355                 360                 365

Lys Arg Ile Gln Glu Ile Ile Glu Gln Leu Asp Val Thr Thr Ser Glu
370                 375                 380

Tyr Glu Lys Glu Lys Leu Asn Glu Arg Leu Ala Lys Leu Ser Asp Gly
385                 390                 395                 400

Val Ala Val Leu Lys Val Gly Gly Thr Ser Asp Val Glu Val Asn Glu
                405                 410                 415

Lys Lys Asp Arg Val Thr Asp Ala Leu Asn Ala Thr Arg Ala Ala Val
            420                 425                 430

Glu Glu Gly Ile Val Leu Gly Gly Cys Ala Leu Leu Arg Cys Ile
            435                 440                 445

Pro Ala Leu Asp Ser Leu Thr Pro Ala Asn Glu Asp Gln Lys Ile Gly
            450                 455                 460

Ile Glu Ile Ile Lys Arg Thr Leu Lys Ile Pro Ala Met Thr Ile Ala
465                 470                 475                 480

Lys Asn Ala Gly Val Glu Gly Ser Leu Ile Val Glu Lys Ile Met Gln
                485                 490                 495

Ser Ser Ser Glu Val Gly Tyr Asp Ala Met Ala Gly Asp Phe Val Asn
            500                 505                 510

Met Val Glu Lys Gly Ile Ile Asp Pro Thr Lys Val Val Arg Thr Ala
            515                 520                 525

Leu Leu Asp Ala Ala Gly Val Ala Ser Leu Leu Thr Thr Ala Glu Val
            530                 535                 540

Val Val Thr Glu Ile Pro Lys Glu Glu Lys Asp Pro Gly Met Gly Ala
545                 550                 555                 560

Met Gly Gly Met Gly Gly Gly Met Gly Gly Met Phe
                565                 570
```

(2) INFORMATION FOR SEQ ID NO:2:

(i) SEQUENCE CHARACTERISTICS:
        (A) LENGTH: 547 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Ala Lys Asp Val Lys Phe Gly Asn Asp Ala Arg Val Lys Met
  1               5                  10                  15

Leu Arg Gly Val Asn Val Leu Ala Asp Ala Val Lys Val Thr Leu Gly
                 20                  25                  30

Pro Lys Gly Arg Asn Val Val Leu Asp Lys Ser Phe Gly Ala Pro Thr
             35                  40                  45

Ile Thr Lys Asp Gly Val Ser Val Ala Arg Glu Ile Glu Pro Glu Asp
 50                  55                  60

Lys Phe Glu Asn Met Gly Ala Gln Met Val Lys Glu Val Ala Ser Lys
 65                  70                  75                  80

Ala Asn Asp Ala Ala Gly Asp Gly Thr Thr Thr Ala Thr Val Leu Ala
                 85                  90                  95

Gln Ala Ile Ile Thr Glu Gly Leu Lys Ala Val Ala Ala Gly Met Asn
            100                 105                 110

Pro Met Asp Leu Lys Arg Gly Ile Asp Lys Ala Val Thr Ala Ala Val
            115                 120                 125

Glu Glu Leu Lys Ala Leu Ser Val Pro Cys Ser Asp Ser Lys Ala Ile
130                 135                 140

Ala Gln Val Gly Thr Ile Ser Ala Asn Ser Asp Glu Thr Val Gly Lys
145                 150                 155                 160

Leu Ile Ala Glu Ala Met Asp Lys Val Gly Lys Glu Gly Val Ile Thr
                165                 170                 175

Val Glu Asp Gly Thr Gly Leu Gln Asp Glu Leu Asp Val Val Glu Gly
            180                 185                 190

Met Gln Phe Asp Arg Gly Tyr Leu Ser Pro Tyr Phe Ile Asn Lys Pro
            195                 200                 205

Glu Thr Gly Ala Val Glu Leu Glu Ser Pro Phe Ile Leu Leu Ala Asp
210                 215                 220

Lys Lys Ile Ser Asn Ile Arg Glu Met Leu Pro Val Leu Glu Ala Val
225                 230                 235                 240

Ala Lys Ala Gly Lys Pro Leu Leu Ile Ile Ala Glu Asp Val Glu Gly
                245                 250                 255

Glu Ala Leu Ala Thr Ala Val Val Asn Thr Ile Arg Gly Ile Val Lys
            260                 265                 270

Val Ala Ala Val Lys Ala Pro Gly Phe Gly Asp Arg Arg Lys Ala Met
            275                 280                 285

Leu Gln Asp Ile Ala Thr Leu Thr Gly Gly Thr Val Ile Ser Glu Glu
            290                 295                 300

Ile Gly Met Glu Leu Glu Lys Ala Thr Leu Glu Asp Leu Gly Gln Ala
305                 310                 315                 320

Lys Arg Val Val Ile Asn Lys Asp Thr Thr Thr Ile Ile Asp Gly Val
                325                 330                 335

Gly Glu Glu Ala Ala Ile Gln Gly Arg Val Ala Gln Ile Arg Gln Gln
            340                 345                 350
```

```
Ile Glu Glu Ala Thr Ser Asp Tyr Asp Arg Glu Lys Leu Gln Glu Arg
            355                 360                 365

Val Ala Lys Leu Ala Gly Gly Val Ala Val Ile Lys Val Gly Ala Ala
            370                 375                 380

Thr Glu Val Glu Met Lys Glu Lys Lys Ala Arg Val Glu Asp Ala Leu
385                 390                 395                 400

His Ala Thr Arg Ala Ala Val Glu Glu Gly Val Val Ala Gly Gly Gly
            405                 410                 415

Val Ala Leu Ile Arg Val Ala Ser Lys Leu Ala Asp Leu Arg Gly Gln
            420                 425                 430

Asn Glu Asp Gln Asn Val Val Ser Ser Ser Leu Arg Ala Met Glu Ala
            435                 440                 445

Pro Leu Arg Gln Ile Val Leu Asn Cys Gly Glu Glu Pro Ser Val Val
            450                 455                 460

Ala Asn Thr Val Lys Gly Gly Asp Gly Asn Tyr Gly Tyr Asn Ala Ala
465                 470                 475                 480

Thr Glu Glu Tyr Gly Asn Met Ile Asp Met Gly Ile Leu Asp Pro Thr
            485                 490                 495

Lys Val Thr Arg Ser Ala Leu Gln Tyr Ala Ala Ser Val Ala Gly Leu
            500                 505                 510

Met Ile Thr Thr Glu Cys Met Val Thr Asp Leu Pro Lys Asn Asp Ala
            515                 520                 525

Ala Asp Leu Gly Ala Ala Gly Met Gly Gly Met Gly Gly Met Gly Met Gly
            530                 535                 540

Gly Met Met
545

(2) INFORMATION FOR SEQ ID NO:3:

(i) SEQUENCE CHARACTERISTICS:
        (A) LENGTH: 540 amino acids
        (B) TYPE: amino acid
        (D) TOPOLOGY: linear (ii) MOLECULE TYPE: protein (xi) SEQUENCE DESCRIPTION: SEQ ID NO:3:

Met Ala Lys Thr Ile Ala Tyr Asp Glu Glu Ala Arg Arg Gly Leu Glu
1               5                   10                  15

Arg Gly Leu Asn Ser Leu Ala Asp Ala Val Lys Val Thr Leu Gly Pro
            20                  25                  30

Lys Gly Arg Asn Val Val Leu Glu Lys Lys Trp Gly Ala Pro Thr Ile
            35                  40                  45

Thr Asn Asp Gly Val Ser Ile Ala Lys Glu Ile Glu Leu Glu Asp Pro
50                  55                  60

Tyr Glu Lys Ile Gly Ala Glu Leu Val Lys Glu Val Ala Lys Lys Thr
65                  70                  75                  80

Asp Asp Val Ala Gly Asp Gly Thr Thr Thr Ala Thr Val Leu Ala Gln
            85                  90                  95

Ala Leu Val Lys Glu Gly Leu Arg Asn Val Ala Ala Gly Ala Asn Pro
            100                 105                 110

Leu Gly Leu Lys Arg Gly Ile Glu Lys Ala Val Asp Lys Val Thr Glu
            115                 120                 125

Thr Leu Leu Lys Asp Ala Lys Glu Val Glu Thr Lys Glu Gln Ile Ala
            130                 135                 140

Ala Thr Ala Ala Ile Ser Ala Gly Asp Gln Ser Ile Gly Asp Leu Ile
```

```
                145                 150                 155                 160
Ala Glu Ala Met Asp Lys Val Gly Asn Glu Gly Val Ile Thr Val Glu
                    165                 170                 175

Glu Ser Asn Thr Phe Gly Leu Gln Leu Glu Leu Thr Glu Gly Met Arg
                180                 185                 190

Phe Asp Lys Gly Tyr Ile Ser Gly Tyr Phe Val Thr Asp Ala Glu Arg
            195                 200                 205

Gln Glu Ala Val Leu Glu Pro Tyr Ile Leu Val Ser Ser Lys
        210                 215                 220

Val Ser Thr Val Lys Asp Leu Leu Pro Leu Leu Glu Lys Val Ile Gln
225                 230                 235                 240

Ala Gly Lys Ser Leu Leu Ile Ile Ala Glu Asp Val Glu Gly Glu Ala
                245                 250                 255

Leu Ser Thr Leu Val Val Asn Lys Ile Arg Gly Thr Phe Lys Ser Val
                260                 265                 270

Ala Val Lys Ala Pro Gly Phe Gly Asp Arg Arg Lys Ala Met Leu Gln
                275                 280                 285

Asp Met Ala Ile Leu Thr Gly Ala Gln Val Ile Ser Glu Glu Val Gly
                290                 295                 300

Leu Thr Leu Glu Asn Thr Asp Leu Ser Leu Leu Gly Lys Ala Arg Lys
305                 310                 315                 320

Val Val Met Thr Lys Asp Glu Thr Thr Ile Val Glu Gly Ala Gly Asp
                325                 330                 335

Thr Asp Ala Ile Ala Gly Arg Val Ala Gln Ile Arg Thr Glu Ile Glu
                340                 345                 350

Asn Ser Asp Ser Asp Tyr Asp Arg Glu Lys Leu Gln Glu Arg Leu Ala
                355                 360                 365

Lys Leu Ala Gly Gly Val Ala Val Ile Lys Ala Gly Ala Ala Thr Glu
                370                 375                 380

Val Glu Leu Lys Glu Arg Lys His Arg Ile Glu Asp Ala Val Arg Asn
385                 390                 395                 400

Ala Lys Ala Ala Val Glu Glu Gly Ile Val Ala Gly Gly Gly Val Thr
                405                 410                 415

Leu Leu Gln Ala Ala Pro Ala Leu Asp Lys Leu Lys Leu Thr Gly Asp
                420                 425                 430

Glu Ala Thr Gly Ala Asn Ile Val Lys Val Ala Leu Glu Ala Pro Leu
                435                 440                 445

Lys Gln Ile Ala Phe Asn Ser Gly Met Glu Pro Gly Val Val Ala Glu
        450                 455                 460

Lys Val Arg Asn Leu Ser Val Gly His Gly Leu Asn Ala Ala Thr Gly
465                 470                 475                 480

Glu Tyr Glu Asp Leu Leu Lys Ala Gly Val Ala Asp Pro Val Lys Val
                485                 490                 495

Thr Arg Ser Ala Leu Gln Asn Ala Ala Ser Ile Ala Gly Leu Phe Thr
                500                 505                 510

Thr Glu Ala Val Val Ala Asp Lys Pro Glu Lys Thr Ala Ala Pro Ala
                515                 520                 525

Ser Asp Pro Thr Gly Gly Met Gly Gly Met Asp Phe
                530                 535                 540

(2) INFORMATION FOR SEQ ID NO:4:

(i) SEQUENCE CHARACTERISTICS:
            (A) LENGTH: 540 amino acids
```

(B) TYPE: amino acid
          (D) TOPOLOGY: linear (ii) MOLECULE TYPE: protein (xi) SEQUENCE DESCRIPTION: SEQ ID NO:4:

Met Ala Lys Thr Ile Ala Tyr Asp Glu Glu Ala Arg Arg Gly Leu Glu
1               5                   10                  15

Arg Gly Leu Asn Ala Leu Ala Asp Ala Val Lys Val Thr Leu Gly Pro
            20                  25                  30

Lys Gly Arg Asn Val Val Leu Glu Lys Lys Trp Gly Ala Pro Thr Ile
        35                  40                  45

Thr Asn Asp Gly Val Ser Ile Ala Lys Glu Ile Glu Leu Glu Asp Pro
50                  55                  60

Tyr Glu Lys Ile Gly Ala Glu Leu Val Lys Glu Val Ala Lys Lys Thr
65                  70                  75                  80

Asp Asp Val Ala Gly Asp Gly Thr Thr Thr Ala Thr Val Leu Ala Gln
                85                  90                  95

Ala Leu Arg Lys Glu Gly Leu Arg Asn Val Ala Ala Gly Ala Asn Pro
            100                 105                 110

Leu Gly Leu Lys Arg Gly Ile Glu Lys Ala Val Glu Lys Val Thr Glu
        115                 120                 125

Thr Leu Leu Lys Gly Ala Lys Glu Val Glu Thr Lys Glu Gln Ile Ala
130                 135                 140

Ala Thr Ala Ala Ile Ser Ala Gly Asp Gln Ser Ile Gly Asp Leu Ile
145                 150                 155                 160

Ala Glu Ala Met Asp Lys Val Gly Asn Glu Gly Val Ile Thr Val Glu
                165                 170                 175

Glu Ser Asn Thr Phe Gly Leu Gln Leu Glu Leu Thr Glu Gly Met Arg
            180                 185                 190

Phe Asp Lys Gly Tyr Ile Ser Gly Tyr Phe Val Thr Asp Pro Glu Arg
        195                 200                 205

Gln Glu Ala Val Leu Glu Asp Pro Tyr Ile Leu Leu Val Ser Ser Lys
    210                 215                 220

Val Ser Thr Val Lys Asp Leu Leu Pro Leu Leu Glu Lys Val Ile Gly
225                 230                 235                 240

Ala Gly Lys Pro Leu Leu Ile Ile Ala Glu Asp Val Glu Gly Glu Ala
                245                 250                 255

Leu Ser Thr Leu Val Val Asn Lys Ile Arg Gly Thr Phe Lys Ser Val
            260                 265                 270

Ala Val Lys Ala Pro Gly Phe Gly Asp Arg Arg Lys Ala Met Leu Gln
        275                 280                 285

Asp Met Ala Ile Leu Thr Gly Gly Gln Val Ile Ser Glu Glu Val Gly
290                 295                 300

Leu Thr Leu Glu Asn Ala Asp Leu Ser Leu Leu Gly Lys Ala Arg Lys
305                 310                 315                 320

Val Val Val Thr Lys Asp Glu Thr Thr Ile Val Glu Gly Ala Gly Asp
                325                 330                 335

Thr Asp Ala Ile Ala Gly Arg Val Ala Gln Ile Arg Gln Glu Ile Glu
            340                 345                 350

Asn Ser Asp Ser Asp Tyr Asp Arg Glu Lys Leu Gln Glu Arg Leu Ala
        355                 360                 365

Lys Leu Ala Gly Gly Val Ala Val Ile Lys Ala Gly Ala Ala Thr Glu
370                 375                 380

```
Val Glu Leu Lys Glu Arg Lys His Arg Ile Glu Asp Ala Val Arg Asn
385                 390                 395                 400

Ala Lys Ala Ala Val Glu Glu Gly Ile Val Ala Gly Gly Gly Val Thr
                405                 410                 415

Leu Leu Gln Ala Ala Pro Thr Leu Asp Glu Leu Lys Leu Glu Gly Asp
            420                 425                 430

Glu Ala Thr Gly Ala Asn Ile Val Lys Val Ala Leu Glu Ala Pro Leu
        435                 440                 445

Lys Gln Ile Ala Phe Asn Ser Gly Leu Glu Pro Gly Val Val Ala Glu
        450                 455                 460

Lys Val Arg Asn Leu Pro Ala Gly His Gly Leu Asn Ala Gln Thr Gly
465                 470                 475                 480

Val Tyr Glu Asp Leu Leu Ala Ala Gly Val Ala Asp Pro Val Lys Val
                485                 490                 495

Thr Arg Ser Ala Leu Gln Asn Ala Ala Ser Ile Ala Gly Leu Phe Leu
            500                 505                 510

Thr Thr Glu Ala Val Val Ala Asp Lys Pro Glu Lys Glu Lys Ala Ser
        515                 520                 525

Val Pro Gly Gly Gly Asp Met Gly Gly Met Asp Phe
    530             535             540
```

STRESS PROTEINS AND USES THEREFOR

RELATED APPLICATIONS

This application is a continuation of application U.S. Ser. No. 08/336,251, filed Nov. 3, 1994, now abandoned, which is a continuation-in-part of the corresponding International Application PCT/US94/06362, filed Jun. 6, 1994 and U.S. Ser. No. 08/073,381, filed Jun. 4, 1993, now abandoned, which is a Continuation-in-Part of U.S. Ser. No. 07/804,632 filed Dec. 9, 1991, now abandoned, which is a File-Wrapper-Continuation of U.S. application Ser. No. 07/366,581 filed Jun. 15, 1989, now abandoned, which is a Continuation-in-Part of U.S. application Ser. No. 07/207,298 filed Jun. 15, 1988, now abandoned, and the corresponding International Application PCT/US89/02619 filed Jun. 15, 1989. The teachings of PCT/US94/06362, U.S. Ser. No. 08/073,381, U.S. Ser. No. 07/804,632, U.S. Ser. No. 07/366,581, U.S. Ser. No. 07/207,298 and PCT/US89/02619 are incorporated herein by reference.

FUNDING

Work described herein was funded by grants from the National Institutes of Health (AI23545), the World Health Organization Program for Vaccine Development, and the World Health Organization/World Bank/United Nations Development Program Special Program for Research and Training in Tropical Diseases. The United States government has certain rights in the invention.

BACKGROUND OF THE INVENTION

Although the function of stress proteins is not entirely clear, it appears that some participate in assembly and structural stabilization of certain cellular and viral proteins, and their presence at high concentrations may have an additional stabilizing effect during exposure to adverse conditions. Neidhardt, F. C. and R. A. Van Bogelen, In: *Escherichia coli* and *Salmonella typhimurium*, Cellular and Molecular Biology, (eds. Neidhardt, F. C., Ingraham, J. L., Low, K. B., Magasanik, B. Schaechter, M. and Umbarger, H. E. (Am. Soc. Microbiol., Washington, D.C.), pp. 1334–1345 (1987); Pelham, H. R. B. *Cell*, 46:959–961 (1986); Takano, T. and T. Kakefuda, *Nature*, 239:34–37 (1972); Georgopoulos, C. et al., *New Biology*, 239:38–41 (1972). Phagocytic host cells produce a hostile environment of foreign organisms, and the ability to produce stress proteins has been implicated in the survival of bacterial pathogens within macrophages Christman, M. F. et al., *Cell*, 41:753–762 (1985).

*Mycobacterium* (*M.*) *tuberculosis* and *Mycobacterium* (*M.*) *leprae* are the etiologic agents of tuberculosis and leprosy, respectively. These diseases afflict 20–30 million people and continue to present a significant global health problem. Joint International Union Against Tuberculosis and World Health organization Study Group, *Tubercle*, 63:157–169 (1982); Bloom, B. and T. Godal, *Rev. Infect Dis.* 5:765–780 (1983). To develop more effective tools for the diagnosis and prevention of these diseases, it is important to understand the immune response to infection by mycobacterial pathogens.

The antibody and T-cell responses to infection or inoculation with killed mycobacteria have been studied in humans and in animals. Human patients with tuberculosis or leprosy produce serum antibodies directed against at least 12 mycobacterial proteins. Some of these proteins are also recognized by well-characterized murine monoclonal antibodies. Mice immunized with mycobacterial lysates produce antibodies that are directed predominantly to six *M. tuberculosis* and six *M. leprae* protein antigens. Engers, H. D. *Infect. Immun.*, 48:603–605 (1985); Engers, H. D., *Infect. Immune.*, 51:718–720 (1986). Genes encoding these 12 mycobacterial antigens have been cloned, and recombinant proteins produced from these clones have been used to investigate the human T-lymphocyte response to mycobacterial infection. Husson, R. N. and R. A. Young, *Proc. Natl. Acad. Sci., USA*, 84:1679–1683 (1987); Young, R. A. et al., *Nature*, 316:450–452 (1985); Britton, W. J. et al., *Lepr. Rev.*, 57, Suppl. 2, 67–75 (1986).

Protection against mycobacterial disease involves cell-mediated immunity. Joint International Union Against Tuberculosis and World Health Organization Study Group, *Tubercle*, 63:157–169 (1982); Hahn, H. and S. H. E. Kaufman, *Rev. Infect. Dis.*, 3:1221–1250 (1981). T-lymphocytes cloned from patients or from volunteers immunized with killed mycobacteria have been tested for their ability to recognize the recombinant mycobacterial proteins. Lymphocyte-proliferation assays demonstrate that most of the antigens identified with monoclonal antibodies are involved in the T-cell response to mycobacterial infection or vaccination in mice and in humans. Limiting dilution analysis indicates that 20% of the mycobacterial-reactive $CD4^+$ T-lymphocytes in mice immunized with M. tuberculosis recognize a single protein, the 65-kDa antigen. Kaufman, S. H. E. et al., *Eur J. Immunol.*, 17:351–357 (1987).

SUMMARY OF THE INVENTION

The present invention relates to stress proteins and methods of modulating an individual's (such as a human, other mammal or other vertebrate) immune response. In particular, it relates to the use of such stress proteins in immune therapy or prophylaxis, which results in an induction or enhancement of an individual's immune response and as an immunotherapeutic agent which results in a decrease of an individual's response to his or her own cells. In the embodiment in which an individual's immune response is induced or enhanced, the induced or enhanced response can be a response to antigens, such as those derived from a pathogen or cancer cell, or can be upregulation of the individual's immune status, such as in an immune compromised individual. In immune prophylaxis, stress proteins are administered to prevent or reduce the effects in an individual of a pathogen, which can be any virus, microorganism, parasite or other organism or substance (e.g., a toxin or toxoid) which causes disease or to prevent or reduce the effects in an individual of cancer cells. In preventing or reducing adverse effects of pathogens which contain stress proteins (e.g., bacteria, parasite, fungus) according to the method of the present invention, an individual's immune response to the pathogen's stress protein(s) is induced or enhanced through the administration of a vaccine which includes the pathogen's stress protein(s) or other stress proteins. The stress protein can be administered alone, as a member or component of a conjugate (e.g., joined to another antigen by chemical or recombinant means such as joined to a fusion partner resulting in a fusion protein), or as an adjuvant or carrier molecule to enhance or obtain a desired immune response to an antigen.

The present invention also relates to compositions which are conjugates comprised of a stress protein joined to another substance or component. For example, the present invention relates to a conjugate in which a stress protein is chemically linked to an antigen, or in which a stress protein is fused to an antigen (e.g., a fusion protein).

The present invention also relates to a method of generating monoclonal or polyclonal antibodies to a substance using a conjugate comprised of a stress protein joined to the substance. In this embodiment, an effective amount of the conjugate (i.e., an amount which results in an immune response in the host) is introduced into a mammalian host which results in production of antibodies to the substance in the host. The antibodies are removed from the host and purified using known techniques (e.g., chromatography).

Preventing or reducing adverse effects of viral pathogens which do or do not contain stress proteins, as well as preventing or reducing the adverse effects of cancer cells according to the present method, is effected by enhancing an individual's immune surveillance system. Enhancement of immune response can be effected by modulating the immune cells by stimulation with a stress protein (e.g., a bacterial stress protein).

In the embodiment in which an individual's immune response is decreased, such as is used in treating autoimmune diseases, stress proteins known to be involved in the autoimmune response are administered to turn down an individual's immune response by tolerizing the individual to the stress proteins. Alternatively, the immune response to stress protein, which is known to occur in autoimmune disease, is reduced by interfering with the ability of immune cells which respond to stress proteins to do so.

A selected stress protein of the present invention can be administered to an individual, according to the method of the present invention, and result in an immune response which provides protection against subsequent infection by a pathogen (e.g., bacteria, other infectious agents which produce stress proteins) or reduction or prevention of adverse effects of cancer cells. Alternatively, a selected stress protein can be administered to an individual, generally over time, to induce immune tolerance against the selected stress protein. For example, a selected stress protein can be administered in multiple doses over time in order to induce immune tolerance against an autoimmune disease such as rheumatoid arthritis.

BRIEF DESCRIPTION OF THE DRAWINGS

FIGS. 2A–2B are a comparison of the amino acid sequence of the human P1 protein (573 residues) (SEQ ID NO: 1) and the amino acid sequence of the groEL protein (547 residues) (SEQ ID NO: 2).

FIGS. 3A–3B are a comparison of the amino acid sequence of the human P1 protein (573 residues) (SEQ ID NO: 1), which is a homolog of groEL protein, and the amino acid sequence of the 65 kDa M. leprae protein (540 residues) (SEQ ID NO: 3).

FIGS. 4A–4B are a comparison of the amino acid sequence of the human P1 protein (573 residues) (SEQ ID NO: 1), which is a homolog of the groEL protein, and the amino acid sequence of the 65kDa M. tuberculosis protein (540 residues) (SEQ ID NO: 4).

FIG. 6 is a schematic representation of the stress protein fusion vector, pKS70 containing the T7 RNA polymerase promoter, a polylinker and the *mycobacterial tuberculosis* hsp70 gene, and the stress protein fusion vector pKS72 containing the HIV p24 gag gene subcloned into the pKS70 vector.

DETAILED DESCRIPTION OF THE INVENTION

Figure 1A:
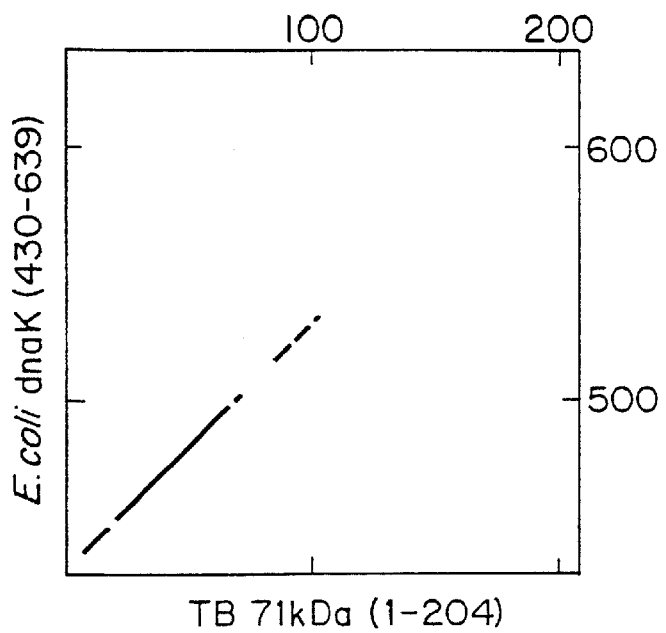
FIG. 1A is a graph illustrating the sequence similarity between portions of the M. tuberculosis 71-kDa antigen (residues 1–204; TB 71 kDa) and the E. coli DnaK protein (residues 430–639).

Cells respond to a variety of stressful stimuli by increasing the synthesis of specific stress proteins. The most extensively studied cellular response to stressful stimuli is the synthesis of heat shock proteins (hsp) by a cell, induced by a sudden increase in temperature. Because many of the heat shock proteins are also induced by other stresses, they are frequently called stress proteins. Stress proteins and their relatives appear to help assemble and disassemble protein complexes. In bacteria, the major stress proteins, hsp70 and hsp60, occur at moderate levels in cells that have not been stressed but accumulate to very high levels in stressed cells. For example, hsp70 and hsp60 normally account for 1–3% of total *E. coli* protein, but can accumulate to about 25% under stressful conditions. Eukaryotic hsp70 and hsp60 proteins do not accumulate to these extreme levels. Their levels range from undetectable to moderately abundant, depending on the organism and cell type.

The present invention is based on the observation that stress proteins are among the major antigens available for presentation to T lymphocytes and may be common immune targets in a broad spectrum of infectious diseases. Immune responses to stress proteins are involved in immune surveillance by the body and a variety of different T cell types has been shown to recognize highly conserved stress protein determinants. Several observations, described below, suggest a model of immune surveillance in which self-reactive T cells provide a first line of defense against infection or other invasion by pathogens, which include, but are not limited to, viruses, microorganisms, other organisms, substances such as toxins and toxoids, and agents which cause cell transformation, by recognizing and helping to eliminate stressed autologous cells, as well as cells infected with intracellular pathogens. Without wishing to be bound by this model, it is presented as one means by which it is possible to explain why prokaryotic and eukaryotic cells respond to a variety of potentially damaging stimuli, such as elevated temperature, by increasing the synthesis of a family of proteins, referred to as stress proteins, which are among the most highly conserved and abundant proteins found in nature.

Investigation of antigens involved in the immune response to the tuberculosis and leprosy bacilli (*M. tuberculosis* and *M. leprae*) initially led to the observation that a variety of stress proteins are among the major targets of the immune response, as is described at greater length below.

Further assessment has demonstrated that stress proteins may be common immune targets in a broad spectrum of infectious diseases. Sequence analysis has revealed 70-kDa heat shock protein homologues among major antigens of the protozoan parasites *Plasmodium falciparum* (Bianco, A. E. et al., *Proc. Natl. Acad. Sci., USA*, 83:8713–8717 (1986)) and *Schistosoma mansoni* (Hedstrom, R. et al., *J. Exp. Med.*, 165:1430–1435 (1987)) and the malarial parasite *Brugia malayi* (Selkirk, M. E. et al., *J. Cell Biochem.*, 12D:290

(1988)). Similarly, homologues of GroEL have been found among antigens involved in the immune response to *Salmonella typhimurium* and *Coxiella* (Vodkin, M. H. and J. C. Williams, *J. Bacteriol*, 170:1227 (1988)), as well as *Bordetella pertussis* (Del Giudice, G., et al., *J. of Imm.*, 150: 2025–2032 (1993)). The presence of stress proteins among major immune targets in a variety of human pathogens is support for the idea that the stress response may be a general component of infection and that stress proteins should be considered among candidates for subunit vaccines. All organisms respond to heat by inducing synthesis of heat shock proteins (hsp), which are a group of proteins. This response is the most highly conserved genetic system known and has been shown to occur in every organism, including microorganisms, plants and animals, investigated to date. Many of the characteristics of the response are common to all organisms and the hsp are among the most highly conserved proteins known. For example, hsp90 family and hsp70 family proteins are present in widely diverse organisms. The proteins in each family—even in such diverse organisms—show approximately 50% identity at the amino acid level and at the nonidentical residues, exhibit many similarities. Several of the proteins induced by heat are also induced by a variety of other stresses. The hsps or a closely related/similar protein are present in all organisms at normal temperatures and have been shown to have key functions in normal cell metabolism. Lindquist, S. and E. A. Craig, *Ann. Rev. Genet.*, 22:631–677 (1988). Because the stress response is common to prokaryotes and eukaryotes and stress proteins are among the most highly conserved in sequence, it is reasonable to expect that an antigen from one pathogen could immunize against another pathogen. Exposure to foreign stress proteins early in life might, in fact, induce a degree of immunity to a variety of infectious agents. If so, this could provide an explanation for the observation that, for many pathogens, only a fraction of infected individuals actually acquire clinical disease.

The following is a description of the relationship which has been observed between stress proteins and the immune response to mycobacterial infection; of the observation and supporting information that stress proteins are immune targets in many infections by pathogens; of the role of stress proteins as immune targets in transformed cells; of recognition of the fact that the immune response to conserved stress protein determinants may play an important role in autoimmune pathology in rheumatoid arthritis, as well as in adjuvant arthritis; and of the role of stress proteins in immune surveillance, as well as a model proposed for immune surveillance in which self-reactive T cells provide a first line of defense against infection and cell transformation.

Mycobacterial Stress Proteins are Targets of the Immune Response

An intriguing relationship between stress proteins and the immune response to mycobacterial infection has been observed. A more detailed examination of stress protein determinants and immune response mechanisms is essential to understanding the relationship among stress proteins, infection, and immunity.

In view of the involvement of proteins of *M. tuberculosis* and *M. leprae* in humoral and cell-mediated immune responses and to establish the functions of these proteins in the mycobacterial cell, the DNA encoding several of the *M. tuberculosis* and *M. leprae* antigens have been sequenced. The results, discussed in Example 1, demonstrate that many of these mycobacterial protein antigens exhibit striking sequence similarity to known stress-induced proteins. Three of the *M. leprae* and two of the *M. tuberculosis* protein antigens studied have been shown to exhibit striking sequence similarity to known stress proteins. For reasons discussed in Example 1, it is concluded that two of the *M. leprae* and two of the *M. tuberculosis* antigens are homologues of the *E. coli* DnaK and GroEL proteins.

In mice, immunization with mycobacterial lysates elicits antibody responses to at least six *M. tuberculosis* protein antigens and a similar number of *M. leprae* protein antigens. Monoclonal antibodies specific for these proteins have been used to isolate clones from λgt11 DNA expression libraries of *M. tuberculosis* and *M. leprae*. The sequence of the DNA clones revealed that mycobacterial hsp70 (alias 70 kDa antigen) and hsp60 (alias 65 kDa antigen, GroEL) were the major targets of the murine antibody response to both *M. tuberculosis* and *M. leprae*. Two additional hsp, an 18 kDa member of the small hsp family and a 12 kDa homologue of groES, were found among the *M. leprae* and *M. tuberculosis* antigens. Young, D. B., et al., *Proc. Natl. Acad. Sci., USA*, 85:4267–4270 (1988); Shinnick, T. M., et al., *Nuc. Acids Res.*, 17:1254 (1989).

The mycobacterial stress proteins are among the immunodominant targets of both murine antibody and T cell responses. In one study which summarized results obtained from 10 laboratories, a collection of 24 murine monoclonal antibodies recognized 6 *M. leprae* proteins; 7 of these antibodies are directed against 6 different determinants in the *M. leprae* hsp60. Engers, H. D., et al., *Infect. Immune.*, 48:603–605 (1985); Mehra, V., et al., *Proc. Natl. Acad. Sci., USA*, 83:7013–7017 (1986). In a similar study, 3 of 33 monoclonal antibodies raised against *M. tuberculosis* recognized the *M. tuberculosis* hsp60 protein. Engers, H. D., et al., *Infect. Immune.*, 1:718–720 (1986). Finally, limiting dilution analysis indicates that 20% of the mycobacterial-reactive CD4+ T lymphocytes in mice immunized with *M. tuberculosis* recognize this antigen. Kaufmann, S. H., et al., *Eur. J. Immunol.*, 17:351–357 (1987).

Although a rigorous quantitative analysis of the human immune response to mycobacterial stress proteins has not yet been reported, mycobacterial stress proteins are recognized by human antibodies and T lymphocytes and the evidence suggests that these proteins are among the major targets of the human cell mediated immune response. Emmrich. F., et al., *J. Exp. Med.*, 163:1024–1029 (1985);. Mustafa, A. S., et al., *Nature* (London). 319:63–66 (1986); Oftung, F., et al., *J. Immunol.*, 138:927–931 (1987); Lamb, J. R., et al., *EMBO J.*, 6:1245–1249 (1987). T lymphocytes from patients with mycobacterial infection or from volunteers immunized with mycobacteria have been cloned and tested for their ability to recognize the mycobacterial stress proteins. In each of these studies, some fraction of the human T cell clones were shown to recognize one or more of the mycobacterial stress proteins.

Stress Proteins are Immune Targets in Infections by Pathogens

The observation that stress proteins are important targets of the immune response to mycobacterial infection and the knowledge that the major stress proteins are conserved and abundant in other organisms suggested that stress proteins are likely to be immune targets in many infections by pathogens. Indeed, that is now clearly the case. Antigens from a wide variety of infectious agents have been identified as members of stress protein families. The major stress protein antigen recognized by antibodies in bacterial infections is hsp60. "Common antigen", an immunodominant protein antigen long known to be shared by most bacterial species, turns out to be hsp60. Shinnick, T. M., et al., *Infect. Immune.*, 56:446 (1988); Thole, J. E. R., et al., *Microbial Pathogenesis*, 4:71–83 (1988). Stress proteins have also been identified as immune targets in most major human parasite infections. Bianco, A. E., et al., *Proc. Natl. Acad. Sci. USA*, 83:8713 (1986); Nene, V., et al., *Mol. Biochem. Parasitol.*, 21:179 (1986); Ardeshir, F., et al., *EMBO J.*, 6:493 (1987); Hedstrom, R., et al., *J. Exp. Med.*, 165:1430 (1987); Selkirk, M. E., et al., *J. Cell Biochem.*, 12D:290 (1988), Engman, D. M., et al., *J. Cell Biochem.*, 12D: Supplement, 290 (1988); Smith, D. F., et al., *J. Cell Biochem.*, 12D:296 (1988). Antibodies to hsp70 have been identified in the sera of patients suffering from malaria, trypanosomiasis, leishmaniasis, schistosomiasis and filariasis. Hsp90 is also a target of antibodies in trypanosomiasis and a member of the small hsp family is recognized in some patients with schistosomiasis.

Proteins homologous to stress proteins have also been identified in viruses. Recently, a protein encoded by the RNA genome of the Beet Yellows Closterovirus, a plant virus, has been shown to be homologous to hsp70. Agranovsky, A. A., et al., *J. Mol. Biol.*, 217: 603–610 (1991). In addition, stress protein induction occurs in eukaryotic cells following infection by diverse viruses in vitro. Collins, P. L., and Hightower, L. E., *J. Virol.*, 44:703–707 (1982); Nevins, J. R., *Cell*, 29:913–939 (1982); Garry, R. F. et al., *Virology*, 129:391–332 (1988); Khandjian, E. W. and Turler, H., *Mol. Cell Biol.*, 3:1–8 (1983); LaThangue, N. B., et al., *EMBO J.*, 3:267–277 (1984); Jindal, S. and Young, R., *J. Viral*, 66:5357–5362 (1992). CTL that recognize these neo-antigens could limit the spread of virus by killing infected cells, possibly before substantial amounts of mature virus are assembled, and by secreting the lymphokine γ-interferon. Pestka, S., in: *Methods Enzymol.*, Interferons, Part A., Vol. 79 Academic Press, New York, pp. 667 (1981). Evidence consistent with this idea is emerging. Koga et al., (1989) have shown that infection of primary murine macrophages with CMV rendered them susceptible as targets for MHC-I restricted $CD8^+$ CTL specific for linear epitopes of *M. tuberculosis* hsp60. Koga, T., et al. (1989). Although the epitope recognized by these CTL on infected macrophages was not defined, it is tempting to speculate that a cross-reactivity with self hsp60 epitopes is being observed. Indeed, the same groups showed that a homologous hsp60 is constitutively present in macrophages and is upregulated by γ-interferon stimulation.

Stress Proteins as Immune Targets in Transformed Cells

Stress proteins appear to be produced at high levels in at least some transformed cells. Bensaude, O. and Morange, M., *EMBO J.*, 2: 173–177 (1983). An 86 kDa murine tumor antigen has been found to be homologous to representatives of the hsp90 family in yeast and Drosophila. Ullrich, S. J., *Proc. Natl. Acad. Sci., USA*, 83: 3121–3125 (1986). Immunization of mice with the purified protein led to inhibition of tumor growth in 95% of experimental animals that had been seeded with cultured tumor cells. All of the protected mice had high titers of anti-hsp90 serum antibody which was able to precipitate murine hsp90 from lysates of heat shocked mouse embryo cells. Again, a role for autoreactive lymphocytes is implied, since T cells capable of recognizing autologous cells stressed by transformation could help eliminate nascent tumor cells.

Stress Proteins and Autoimmune Processes

Rheumatoid arthritis is characterized by a chronic proliferative and inflammatory reaction in synovial membranes which is thought to involve autoimmune processes. Rat adjuvant arthritis resembles human rheumatoid arthritis in many respects, and has been used as an experimental animal model for human disease. Pearson, C. M., *Arthritis Rheum.*, 7:80–86 (1964). Adjuvant arthritis can be induced in rats with a single intradermal injection of killed *M. tuberculosis* in complete Freund's adjuvant. An autoimmune process involving T lymphocytes appears to be responsible for the generation of the disease. Holoshitz, J., et al., *Science*, 219:56–58 (1983). T cell lines isolated from the draining lymph nodes of arthritic rats and propagated in vitro by stimulation with *M. tuberculosis*-pulsed syngeneic antigen presenting cells can cause a transient form of the disease when transferred to irradiated rats. Since care was taken in these experiments to exclude the transfer of contaminating *M. tuberculosis*, this result strongly suggests that the clinical effects of the disease are a consequence of an autoimmune reaction in which the autoantigen is shared with *M. tuberculosis*.

The rat and *M. tuberculosis* antigens recognized by the arthritogenic T cells have been sought for a number of years. A number of different proteins present in synovial membranes have been proposed to be the cross-reactive rat antigen, but were later discounted as procedures for the purification of these proteins improved. van Eden, W., et al., *Proc. Natl. Acad. Sci., USA*, 82:5117–5120 (1985); Holoshitz, J., et al., *Science*, 219:56–58 (1983). The *M. tuberculosis* antigen recognized by the arthritogenic T cells was recently shown to be a 65 kDa protein (van Eden, W., et al., *Nature*, 331:171 (1988), which has now been shown to be hsp60 (see the Example 1). Using a combination of truncated recombinant 65 kDa proteins and peptides, a nine amino acid epitope of hsp60 has been identified as the minimum stimulatory sequence for arthritogenic T cell clones in proliferation assays. Now that it is clear that some arthritogenic T cells recognize the mycobacterial hsp60, it is quite possible that the rat autoantigen is also hsp60.

The results obtained in the adjuvant arthritis model led investigators to determine whether T lymphocytes from human rheumatoid arthritis patients also recognize mycobacterial antigens. These investigators have found not only that patients with rheumatoid arthritis have T cells that recognize *M. tuberculosis* antigens, but that these T cells have diverse phenotypes. Substantial proliferative responses to mycobacterial extracts are observed with uncloned T cells (predominantly $CD4^+$) from both synovial infiltrates and peripheral blood, although responses are generally greater in synovial infiltrates. Abrahamson, T. G., et al., *Scand. J. Immunol.*, 7:81–90 (1978); Holoshitz, J., et al., *Lancet ii*, 305–306 (1986). Holoshitz et al. found that 4 of 5 T cell clones isolated from human rheumatoid synovia which respond to *M. tuberculosis* antigens were $CD4^-$ $CD8^-$ cells with γ/δ T cell receptors. Holoshitz, J., et al., *Nature*, 339:226–229 (1989). This observation is interesting because γ/δ T cells have yet to be assigned a role in immunity. One of the γ/δ clones was tested for its ability to respond to purified mycobacterial hsp60 and was found to be positive in proliferation assays. Due to the conserved nature of stress proteins, these T cells have the potential for autoreactivity. Lamb and coworkers have shown that polyclonal T cells from synovial infiltrates recognize both mycobacterial hsp60 and hsp70. Lamb, J. R., et al., *Intl. Immunol.*, in press (1989). The population of T cells that recognize the mycobacterial stress proteins were shown to respond to *E. coli* hsp60 and hsp70 and, most interestingly, human hsp70 purified from heat shocked macrophages. Thus, immune responses to conserved stress protein determinants, perhaps initiated by bacterial infection (not necessarily by mycobacteria), may play an important role in autoimmune pathology in rheumatoid arthritis, as well as in adjuvant arthritis.

Stress Proteins and Immune Surveillance

A variety of different T cell types has now been shown to recognize highly conserved stress protein determinants. The ability of cells to respond to stress by increasing the levels of the highly conserved stress proteins; the presence of T cells of diverse phenotypes in healthy individuals that are capable of recognizing self stress protein determinants; and observations that stress responses are induced by pathogenic infections and by cell transformation, all suggest a model of immune surveillance in which self-reactive T cells provide a first line of defense against infection and transformation by recognizing and helping to eliminate stressed autologous cells, as well as cells infected with intracellular pathogens. The pool of lymphocytes that recognize conserved stress protein determinants might be induced during establishment of natural microbial flora on the skin and in the gut, and maintained by frequent stimulation by pathogens, such as bacteria and viruses, as well as other stressful stimuli encountered during a normal lifetime. This model is attractive because it provides a way in which the immune system could exploit the existence of conserved epitopes in stress proteins to respond immediately to antigenically diverse pathogens and cellular changes, producing an initial defense that need not await the development of immunity to novel antigens.

The lymphocytes which recognize conserved stress protein determinants must be capable of discriminating between normal and stressed cells. Since many stress proteins are constitutively expressed in normal cells, although at lower levels than in stressed cells, the potential for autoreactivity is ever-present. Normal cells may escape destruction by expressing only substimulatory levels of stress protein determinants on their surfaces. In addition, stress proteins may only be processed and presented during stress, and it may be relevant that many stress proteins have altered intracellular locations during stress. Finally, immune regulatory networks may prevent activation of autoreactive T cells under normal conditions. The regulatory constraints required by this system might occasionally break down, perhaps during stress caused by bacterial or viral infections, leading to autoimmune disease. Rheumatoid arthritis may be such a disease.

Modulation of Immune Response

The precise relationship between stress proteins and the host immune response to infection is as yet undefined. When cells are subjected to a variety of stresses, they respond by selectively increasing the synthesis of a limited set of stress proteins. Some stress proteins, including the products of DnaK and GroEL, are major constituents of the cell under normal growth conditions and are induced to even higher levels during stress. Lindquist, S., *Annu. Rev. Biochem.* 55: 1151–1191 (1986); Neidhardt, F. C. and R. A. VanBogelen, In *Escherichia coli* and *Salmonella TVphimurium*, Cellular and Molecular Biology, (eds. Neidhardt, F. C., Ingraham, J. L. Low, K. B. Magasanik, B. Schaechter, M. and Umbarger, H. E.) Am. Soc. Microbiol., Washington, D.C., pp. 1134–1345 (1987). It has now been demonstrated that stress-related proteins are targets of the immune response. Young, D. et al., *Proc. Natl. Acad. Sci. USA*, 85:4267–4270 (1988). It is reasonable to expect that immunodominant antigens would be found among such abundant proteins, as has now been shown to be the case.

According to the method of the present invention, it is possible to modulate the immune response in an individual, such as a human, other mammal or other vertebrate, by altering the individual's response to stress proteins. In particular, it is possible to enhance or induce an individual's response to a pathogen (e.g., bacteria, virus, parasites, or other organism or agent, such as toxins, toxoids) or to cancer cells or enhance or induce an upregulation of an individual's immune status (such as in an immune compromised individual or HIV-infected individual); and to decrease an individual's autoimmune response, such as occurs in some forms of arthritis. In addition, administration of a stress protein using the method of the present invention provides protection against subsequent infection by a pathogen. As demonstrated herein, stress proteins contain regions of highly conserved amino acid sequences and have been shown to be major immunodominant antigens in bacterial and other infections. Therefore, it is reasonable to expect stress proteins can be used to elicit strong immune responses against a variety of pathogens. The stress protein administered to induce or enhance an immune response to pathogens can be the stress protein of the pathogen against which an immune response is desired or other stress protein, a portion of that protein of sufficient size to stimulate the desired immune response or a protein or amino acid sequence which is the functional equivalent of the stress protein in that it is sufficiently homologous in amino acid sequence to that of the stress protein to be capable of eliciting the desired response (an immune response substantially similar to that which occurs in response to the stress protein) in the individual to whom it is administered. The term "sufficiently homologous in amino acid sequence to that of the stress protein" means that the amino acid sequence of the protein or polypeptide will generally show at least 40% identity with the stress protein amino acid sequence; in some cases, the amino acid sequence of a functional equivalent exhibits approximately 50% identity with the amino acid sequence of the stress protein.

Any stress-induced proteins or their functional equivalents can be used by the present invention to enhance or induce an immune response in an individual (e.g. a human, other mammal or vertebrate), against an infection by a pathogen, for immunotherapy against cancer cells, for generally upregulating an individual's immune status and for use in inducing immune tolerance in an individual or animal.

The stress proteins of the present invention can be administered in a variety of ways to modulate the immune response of an individual (e.g., a human, other mammal or other vertebrate). In one embodiment, the stress protein is administered as a vaccine which is comprised of the stress protein or a portion of the stress protein which is of sufficient size to stimulate the desired immune response. In this embodiment, the vaccine can be a "specific vaccine" which contains a specific stress protein of a particular pathogen against which an immune response is desired, such as a bacterial stress protein. In this case, since the pathogen's stress proteins are distinguishable from those of the host, it is possible to induce an immunoprophylactic response specific to the pathogen's stress proteins. Blander, S. J., et al., *J. Clin. Invest.*, 91:717–723 (1993). This can be carried out by administering a vaccine which includes all or a portion (e.g., sufficient amino acid sequence to have the desired stimulatory effect on immune response) of the pathogen's stress protein or of another protein having an amino acid sequence sufficiently similar to that of the stress protein sequence to stimulate the immune response to the pathogen's stress protein. Alternatively, in the case of a pathogen which does not contain stress proteins, (e.g. some viruses) or in the condition of neoplasia, stress proteins or highly conserved stress protein determinants, such as those shown to be recognized by a variety of T cells, can be administered as a type of "general" vaccine to achieve an upregulation of the immune response. Administration of such a vaccine will enhance the existing immune surveillance system. For instance, a vaccine which includes a bacterial, or other stress protein can be administered to enhance the immune system which will result in an immune response against a pathogen which does not contain stress proteins. Alternatively, this type of "general" vaccine can be used to enhance an individual's immune response against cancer or to generally upregulate an individual's immune status, such as in an immune compromised individual (e.g., an individual undergoing chemotherapy or an HIV-infected individual). In either case of this embodiment (specific or general vaccine), the immune response to the stress protein sequence will be increased and effects of the pathogen, disease condition or immune impairment will be reduced (decreased, prevented or eliminated).

In another embodiment, stress proteins can be used to enhance immune surveillance by applying local heat or any other substances or changes in condition which induce the stress response in the individual being treated. (This can also be employed in conjunction with the specific vaccine, described previously, administered to enhance an immune response to a stress protein-containing pathogen or in conjunction with the general vaccine, described above, administered to enhance the immune response against a pathogen which does not contain its own stress proteins, cancer, or to upregulate the immune status of an individual). For example, it is known that increased levels of stress proteins are produced in many types of cancer cells. Therefore, enhancement of the immune surveillance system, using this embodiment of the present invention as described, can be used to facilitate destruction and/or to prevent progression or establishment of cancer cells.

The method of the present invention can also be used to modify or modulate an individual's response to his or her own cells (e.g., as in autoimmune diseases). There are at least two ways in which the present invention can be used immunotherapeutically. First, stress proteins, such as heat shock proteins (e.g., hsp 70 and hsp60 ), are known to be involved in autoimmune disease. It is, thus, possible to turn down an individual's immune response, resulting in the individual becoming more tolerant of the protein. Second, because it is known that under some circumstances, one component of the immune response in certain autoimmune diseases can be to stress proteins, it is possible to selectively inhibit or interfere with the ability of immune cells which normally interact with such proteins to do so. This can be done, for example, by administering monoclonal antibodies that bind to specific T cell receptors and delete or disable such cells. Alternatively, rather than knocking out immune cells, the stress response in cells can be turned down by administering a drug capable of reducing a cell's ability to undergo the stress response. For example, a drug targeted to or specific for heat shock transcription factor, which is needed to stimulate heat shock genes, can be administered. The transcription factor is rendered nonfunctional or subfunctional and, as a result, cells' ability to undergo the stress response is also lessened.

In another embodiment of the present invention, the stress protein is administered as a vaccine which is comprised of two moieties: a stress protein and another substance (referred to as an antigen, e.g. protein, peptide, carbohydrate, lipid, organic molecule) against which an immune response is desired. The two moieties are conjugated or joined to form a single unit. Conjugation can be achieved by chemical means known to those skilled in the art (e.g. through a covalent bond between the stress protein and the second moiety; reductive amination) or, as demonstrated in Example 2, by recombinant techniques. If recombinant techniques are used to produce the conjugate, the result is a recombinant fusion protein which includes the stress protein and the antigen in a single molecule. This makes it possible to produce and purify a single recombinant molecule in the vaccine production process. In this embodiment, the stress protein can be seen to act as an adjuvant-free carrier, and it stimulates strong humoral and T cell responses to the substance to which the stress protein is fused. The stress protein can be conjugated to any substance against which an immune response is desired or to a portion of the substance sufficient to induce an immune response in an individual to whom it is administered. The substance includes but is not limited to proteins (e.g., ovalbumin, Influenza virus Hemagglutinin, Human Immunodeficiency Virus p24), peptides (e.g., Human Immunodeficiency Virus peptides, melanoma antigen peptides), oligosaccharides (e.g., Neiserria meningitidis group B, Streptococcus pneumoniae type 14, Hemophilis influenzae type b), lipids, carbohydrates (e.g., glycolipid antigens in human cancers such as GD3, GM2, Gb3, Forssman antigen, Sialosyl-Le$^a$ antigen and glycoprotein antigens in human cancers such as CEA, AFP, PSA, Tn antigen), organic molecules or a combination thereof. Recent evidence demonstrating the effectiveness of such a vaccine indicates that mycobacterial hsp70 proteins when conjugated to other proteins act as adjuvant-free carriers. The humoral immune response to some peptides conjugated to mycobacterial hsp70 administered without any adjuvant was very similar to the antibody response to the same peptides administered in Freund's complete adjuvant. Lussow, A. R., et al., Eur. J. Immune., 21:2297–2302 (1991). Barrios, C. et al., Eur. J. Immune., 22:1365–1372 (1992).

The present: invention also relates to compositions which are conjugates comprised a stress protein joined to another substance or component. For example, the present invention relates to a conjugate in which a stress protein is chemically linked to an antigen, or in which a stress protein is fused to an antigen (e.g., a fusion protein).

Figure 7:
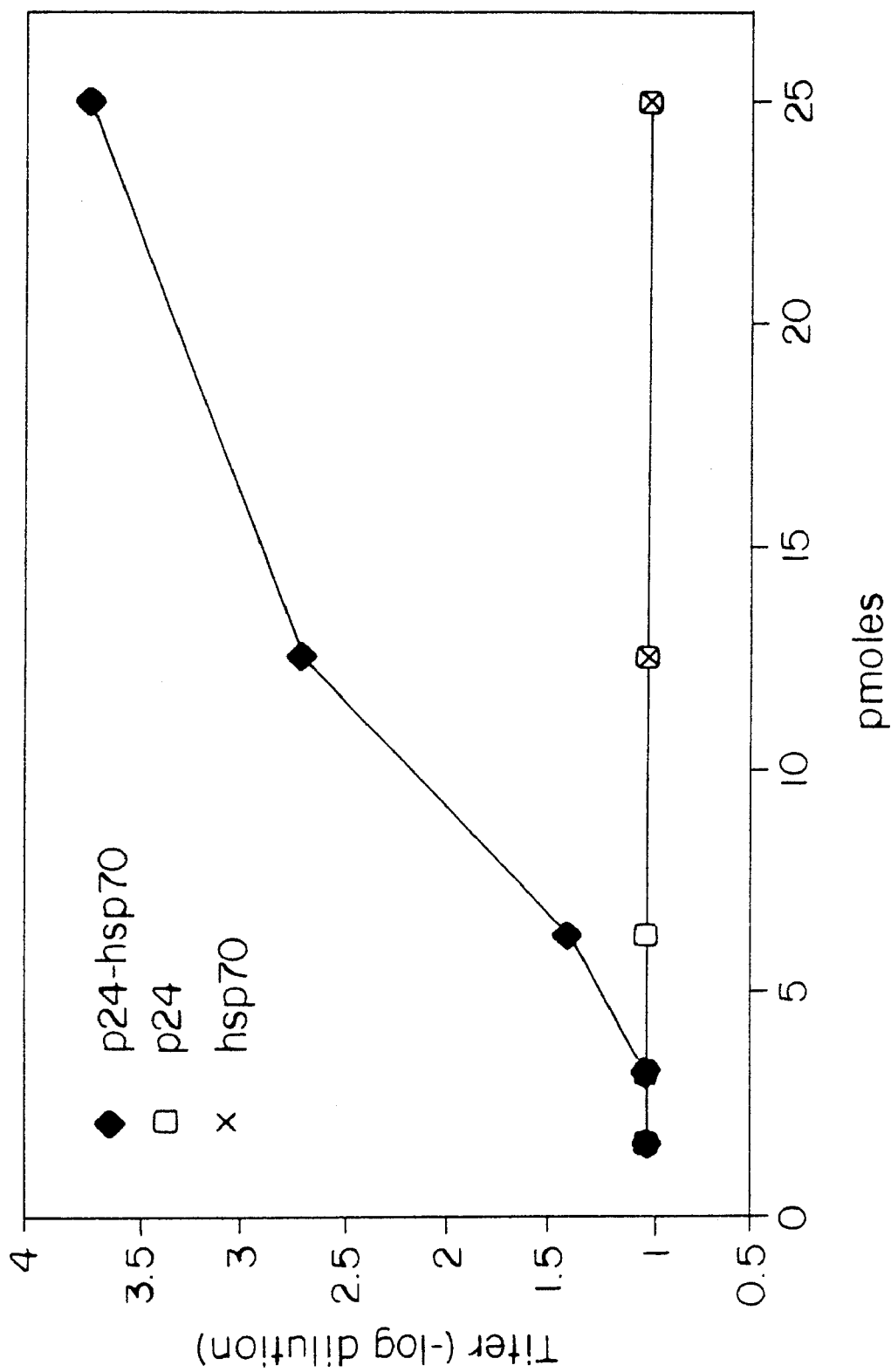
FIG. 7 is a graph illustrating the anti-p24 antibody titer in mice injected with the p24-hsp70 fusion protein, p24 alone and hsp70 alone.

As demonstrated in Example 3, the HIV p24 gag gene was subcloned into the stress protein fusion vector pKS70 (FIG. 6), containing the T7 RNA polymerase promoter, a polylinker and the mycobacterial tuberculosis hsp70 gene. The resulting vector pKS72 (FIG. 6) was used to produce the p24-hsp70 fusion protein in E. coli. Adjuvant-free, purified p24-hsp70 fusion protein was injected into Balb/c mice and as shown in FIG. 7, the anti-p24 antibody titer was 2.7 orders of magnitude higher in mice injected with the p24-hsp70 fusion protein than in mice injected with p24 alone or hsp70 alone. Mice injected with p24 and the adjuvant, alum, also produced an antibody response to p24. Finally, a demonstrable T cell response was seen in mice injected with the p24-hsp70 fusion protein and in mice injected with p24 alone.

In another embodiment of the present invention, the stress protein or a portion of the stress protein which is of sufficient size to stimulate an immune response or an equivalent, is administered as an adjuvant, with another substance (referred to as an antigen) against which an immune response is desired. The stress protein can be used as an adjuvant with any substance or antigen against which an immune response is desired or to a portion of the substance sufficient to induce an immune response in an individual to whom it is administered. The substance includes proteins, peptides, oligosaccharides, lipids, carbohydrates, organic molecules or a combination thereof. Via linkage to a stress protein, strong and specific B and T cell mediated immunity can be generated in a mammalian host (e.g., mice, rabbits, humans) to virtually any organic molecule. This is particularly useful 1) with substances (e.g., antigens) which alone are non-immunogenic; 2) when adjuvants cannot be used or do not work well in combination with a particular antigen; 3) when the availability of purified antigen is limited, particularly with fusion proteins where the antigen is made using recombinant DNA technology; 4) where other carrier molecules, such as KLH, BSA, OVA or thyrogloulin, which additionally require adjuvants, are not effective or desirable; 5) there is a genetic restriction in the immune response to the antigen; 6) there is a pre-existing immunosuppression or non-responsiveness to an antigen (e.g., pediatric vaccines where infants and children under 2 years of age do not generate protective immunity to carbohydrate antigens well); and 7) the type of immune response achieved by other carriers or adjuvants is undesirable or ineffectual (i.e., stress protein conjugates could be used to bias toward either B or T cell immunity via proper dose, route and inoculation regimen).

The present invention also relates to a method of generating monoclonal or polyclonal antibodies to a substance using a conjugate comprised of a stress protein joined to the substance. In this embodiment, an effective amount of the conjugate (i.e., an amount which results in an immune response in the host) is introduced into a mammalian host which results in production of antibodies to the substance in the host. The antibodies are remvoed from the host and purified using known techniques (e.g., chromatography), thereby resulting in production of polyclonal antibodies. Alternatively, the antibodies produced using the method of the present invetion can be used to generate hybridoma cells which produce monoclonal antibodies using known techniques (Kohler, G., et al., *Nature*, 256:495(1975) Milstein et al., *Nature*, 266:550–552(1977); Koprowski et al., *Proc. Natl. Acad. Sci*, 74:2985–2988 (1977); Welsh, *Nature*, 266:495(1977); Maniatis, T. et al., *Molecular Cloning*, A Laboratory Manual, Cold Spring Harbor Lab., Cold Spring Harbor, N.Y. (1982)).

The stress protein, stress protein portion, stress protein functional equivalent and the substance to which the stress protein is fused or conjugated present in the vaccine can be produced or obtained using known techniques. For example, the stress protein or stress protein portion can be obtained (isolated) from a source in which it occurs in nature, can be produced by cloning and expressing a gene encoding the desired stress protein or stress protein portion or can be synthesized chemically or mechanically.

An effective dosage of the stress proteins of the present invention as vaccines or adjuvants, to elicit specific cellular and humoral immunity to stress proteins, or to substances conjugated to the stress proteins, such as proteins or oligosaccharides, is in the range of 0.1 to 1000 ug hsp per injection, depending on the individual to whom the stress protein is being administered. Lussow, A. R., et al., *Eur. J. Immune.*, 21:2297–2302 (1991). Barrios, C. et al., *Eur. J. Immune.*, 22:1365–1372 (1992). The appropriate dosage of the stress protein for each individual will be determined by taking into consideration, for example, the particular stress protein being administered, the type of individual to whom the stress protein is being administered, the age and size of the individual, the condition being treated or prevented and the severity of the condition. Those skilled in the art will be able to determine using no more than routine experimentation, the appropriate dosage to administer to an individual.

Various delivery systems can be used to administer an effective dose of the vaccine of the present invention. Methods of introduction include, for example, intradermal, intramuscular, intraperitoneal, intravenous, subcutaneous, intranasal, epidural and oral routes. Any other convenient route of administration can be used (infusion of a bolus injection, infusion of multiple injections over time, absorption through epithelial or mucocutaneous linings such as, oral mucosa, rectal and intestinal mucosa) or a series of injections over time.

The present invention is further illustrated by the following exemplification, which is not intended to be limiting in any way.

EXEMPLIFICATION

EXAMPLE 1

Isolation and Characterization of Mycobacterial Stress Protein Antigens

Recombinant DNA Clones. The isolation and characterization of *M. tuberculosis* and *M. leprae* λgt11 genomic DNA clones with murine monoclonal antibodies have been described. Husson, R. N. and Young, R. A., *Proc. Natl. Acad. Sci., USA* 84: 1679–1683 (1987); Young, R. A., et al., *Nature* (London) 316: 450–452 (1985). DNA was isolated from these clones and was manipulated by standard procedures. Davis, R. W., *Advanced Bacterial Genetics*: A Manual for Genetic Engineering (Cold Spring Harbor Lab., Cold Spring Harbor, N.Y.), (1980).

DNA Sequence Analysis. DNA was subcloned into vector M13mp18 or M13mp19 (New England Biolabs), as suggested by the supplier. Dideoxynucleotide chain-termination reactions and gel electrophoresis of the sequenced produced were as described. Davis, R. W., *Advanced Bacterial Genetics*: A Manual for Genetic Engineering (Cold Spring Harbor Lab., Cold Spring Harbor, N.Y.), (1980). DNA sequences were determined for both strands of DNA. Computer analysis of sequences with UWGCG programs was as described by Devereux, J., et al., *Nucleic Acids Res.*, 12: 387–395 (1984).

Immunoblot Analysis. *Escherichia coli* strain TG1 was transformed with the following plasmids by standard procedures (Maniatis, T., et al., *Molecular Cloning*, A Laboratory Manual (Cold Spring Harbor Lab., Cold Spring Harbor, N.Y.) (1982), with selection for ampicillin resistance: pND5, a derivative of pBR325 containing the *E. coli* GroEL genes (Jenkins, A. J., et al., *Mol. Gen. Genet.*, 202: 446–454 (1986); pUC8 (Vic, J., *Gene*, 19: 259–268 (1982); pUC8 with insert DNA for λgt11 clone Y3178 (*M. leprae* 65-kDa antigen, Young, R. A., et al., *Nature*, (London) 316: 450–452 (1985)) ligated in the EcoRI site.

Overnight cultures of *E. coli* strains in Luria-Bertani (LB) medium were centrifuged and resuspended in isotonic phosphate-buffered saline at a cell density corresponding to an absorbance of 2 at 600 nm. An equal volume of sample buffer containing 2% (wt/vol) $NaDodSo_4$ was added, and, after heating on a boiling water bath for 2 min, samples were electrophoresed on 12% (wt/vol) polyacrylamide gels in the presence of $NaDodSO_4$. Blots were prepared by electrophoretic transfer of the proteins to a nitrocellulose membrane, and binding of monoclonal antibodies was assayed with a peroxidase-conjugated secondary antibody as described. Young, D. B., et al., *Infect. Immune.*, 55: 1421–1425 (1987).

Six *M. tuberculosis* and six *M. leprae* proteins have been implicated in the immune response to the mycobacterial pathogens (Table 1). To obtain clues to the normal cellular function of several of these mycobacterial antigens, DNA clones encoding these proteins, isolated by using monoclonal antibodies to probe lambda gtll libraries (Husson, R. N. and Young, R. A., *Proc. Natl. Acad. Sci., USA*, 84: 1679–1683 (1987); Young, R. A., et al., *Nature*, (London) 316: 450–452 (1985)) were subjected to sequence analysis. The sequences elucidated have been submitted to the GenBank sequence database.

The Mycobacterial 71-k Da Antigen. The 71-k Da antigen of *M. tuberculosis* is recognized by human T cells during infection (Table 1).

TABLE 1

MYCOBACTERIAL PROTEIN ANTIGENS

| Protein, kDA | Recognized by Human T Cells | Subjected to sequence analysis | Homology with known proteins |
|---|---|---|---|
| *M. tuberculosis* | | | |
| 71 | + | + | DnaK |
| 65* | + | + | GrOEL |
| 38 | + | − | − |
| 19 | + | + | None |
| 14 | + | − | − |
| 12 | ND | − | − |
| *M. leprae* | | | |
| 70 | ND | − | DnaK |
| 65 | + | + | GroEL |
| 36 | + | − | − |
| 28 | + | − | − |
| 18 | + | + | Plant Hsp |
| 12 | ND | − | − |

Mycobacterial protein antigens, their recognition by human T cells, and homology of the deduced mycobacterial protien sequences to known proteins are summarized. ND, not determined; +, yes; −, no Includes data derived from study of the 65-kDA antigens of *M. bovis* BCG (Bacillus Calmette-Gurein), which is identical to the *M. tuberculosis* 65-kDA antigen.

A. S. Mustafa, J. R. Lamb, D. Young and R. A. Young, unpublished data.

The insert DNA of lambdagtll clone Y3271 (Husson, R. N., et al, *Proc. Natl. Acad. Sci, USA*, 84: 1679–1683 (1987), was sequenced to obtain amino acid sequence information for the 71-kDa antigen of *M. tuberculosis*. This clone produces a beta-galactosidase fusion protein containing the carboxyl-terminal one-third of the 71-kDa antigen exhibiting 40% amino acid sequence identity with the comparable segment of the dnaK gene product from *E. coli* (Bardwell, J. C., et al., *Proc. Natl. Sci., USA*, 81: 848–852 (1984)), (FIG. 1). FIG. 1A shows the extent of sequence similarity between portions of the mycobacterial and the *E. coli* 70-k Da polypeptides. Sequences transcriptionally downstream from the mycobacterial 71-k Da gene predict a 356-amino acid protein homologous to the *E. coli* dnaJ gene product (unpublished data), indicating that the *E. coli* dnaK-dnaj operon structure is conserved in *M. tuberculosis* and consistent with the conclusion that the mycobacterial 71-kDa antigen is a homologue of the *E. coli* dnaK gene product. The product of the dnaK gene is a member of the 70-kDa heat shock protein family that is highly conserved among prokaryotes and eukaryotes (Bardwell, J. C., et al., *Proc.* *Natl. Acad. Sci., USA*, 81: 848–852 (1984); Lindquist, S., *Annu. Rev. Biochem.*, 55: 1151–1191 (1986).

The *M. leprae* 70-k Da antigen cross-reacts with monoclonal antibodies directed to the *M. tuberculosis* 70-kDa antigen. *M. tuberculosis* and *M. leprae* are both members of the 70-k Da heat shock protein family of stress proteins.

The mvcobacterial 65-kDa antigen. The 65-kDa antigens of *M. tuberculosis* and *M. leprae* are involved in the human T-cell response to mycobacterial infection (Table 1). Genes encoding these proteins have been isolated (Husson, R. N., and Young, R. A., *Proc. Natl. Acad. Sci., USA*, 84: 1679–1683 (1987); Young, R. A., et al., *Nature*, (London) 316: 450–452 (1985)) and sequenced (Shinnick, T. M., *J. Bacteriol.*, 169: 1080–1088 (1987); Mehram, V., et al., *Proc. Natl. Acad. Sci., USA* 83: 7013–7017 (1986)), revealing that the amino acid sequences of the 65-kDa antigens of *M. tuberculosis* (SEQ ID NO: 4) and *M. leprae* (SEQ ID NO: 3) are 95% identical. These proteins sequences exhibited no significant sequence similarity to proteins in the GenBank database.

Figure 1B:
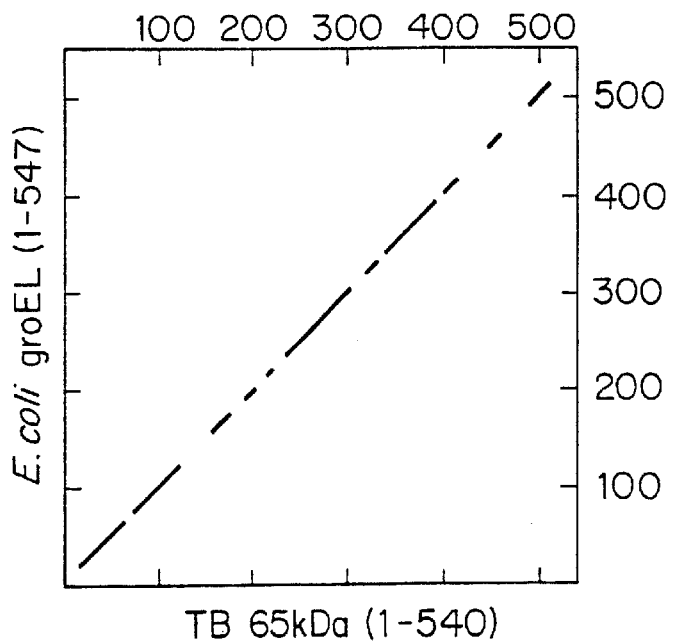
FIG. 1B is a graph illustrating the sequence similarity between portions of the M. tuberculosis 65-kDa antigen (residues 1–540; TB 65 kDa) and the E. coli GroEL protein (residues 1–547).

Identification of these proteins was based on the observation that some monoclonal antibodies directed against the mycobacterial 65-kDa antigens cross-react with an *E. coli* protein of 60 kDa. *E. coli* cells transformed with the plasmid pND5 (Sanger, F., et al., *Proc. Natl. Acad. Sci., USA* 74: 5463–5467 (1977), which contains the *E. coli* gro E genes, had been shown to accumulate large amounts of the 60-kDa protein. A comparison of the mycobacterial 65-kDa protein sequences with those determined for *E. coli* groEl (C. Woolford, K. Tilly, C. Georgopoulous, and R. H., unpublished data) revealed the extent of the sequence similarity as shown in FIG. 1B.

The 60-kDa Gro EL protein is a major stress protein in *E. coli*. Lindquist, S., *Annual. Rev. Biochem.*, 55: 1151–1191 (1986); *Nature*, 333: 330–334 (1988). There is some evidence that the mycobacterial 65-kDa proteins accumulate in response to stress: *Mycobacterium bovis* BCG (bacillus Calmette-Guerin) cultures grown in zinc-deficient medium are substantially enriched in this protein (De Bruyn, J., et al., *Infect. Immune.* 55: 245–252 (1987)). This infers that the 65-kDa proteins of *M. tuberculosis* and *M. leprae* are homologues of the *E. coli* Gro EL protein.

Other Mycobacterial Antigens. T lymphocytes that respond to the *M. tuberculosis* 19-kDa antigen and the *M. leprae* 18-kDa antigen have been observed in humans with tuberculosis and leprosy, respectively (Table 1). DNA encoding these antigens was sequenced from the λgtll clones Y3148 (Husson, R. N. and Young, R. A., *Proc. Natl. Acad. Sci., USA* 84: 1679–1683 (1987); and Y3179 (Young, R. A., et al., *Nature*, (London) 316: 450–452 (1985)), respectively. The *M. tuberculosis* 19-kDa protein sequence predicted from the DNA exhibited no significant sequence similarity to proteins in the GenBank database.

However, the *M. leprae* 18-kDa protein sequence was similar to the soybean 17-kDa protein heat shock protein, a protein representation of a major class of plant heat. shock proteins (Schoffl, F. and Van Bogelen, R. A., In: *Escherichia coli* and *Salmonella typhimurium*, Cellular and Molecular Biology, Am. Soc. Microbiol., Washington, D.C. (1987).

EXAMPLE 2

Figure 5:
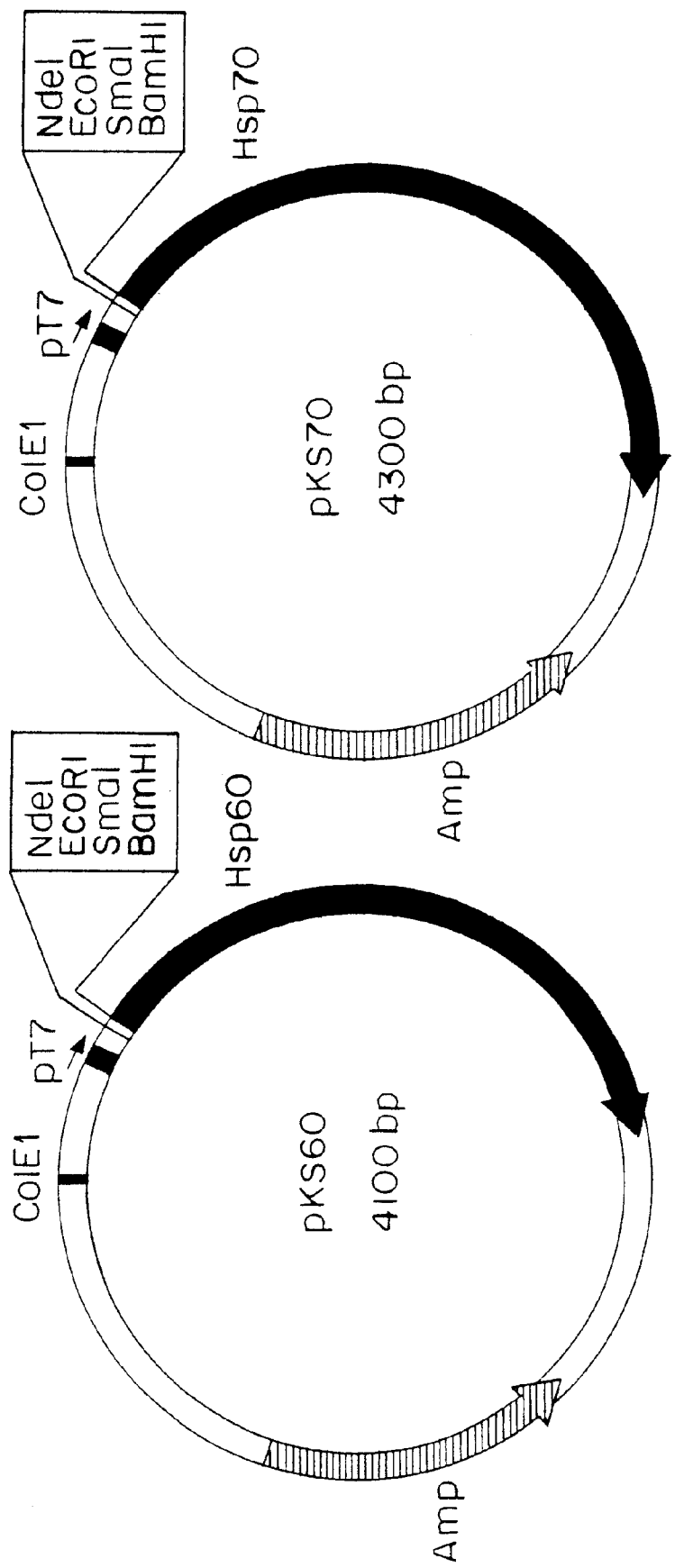
FIG. 5 is a schematic representation of selected stress protein fusion vectors which contain a polylinker with multiple cloning sites permitting incorporation of a gene of interest.

Construction of Stress Protein-Fusion Vaccines for Use as Adjuvant-Free Carriers in Immunizations Recombinant Fusion Vectors. A series of stress protein fusion vectors for use in *E. coli* were constructed and are shown in FIG. 5. These vectors contain the T7 RNA polymerase promoter fused to the *M. bovis* BCG hsp70 gene or the *M. bovis* BCG hsp60 gene. The vectors also contain a polylinker with multiple cloning sites, permitting incorporation of a gene of interest so that the antigen encoded by that gene is expressed as a fusion protein with the stress protein. A subset of these vectors permit incorporation of the foreign gene with a coding sequence for a C-terminal 6-Histidine "tag" for ease of fusion protein purification. Thus far, recombinant clones have been generated that produce hsp70 proteins fused to HIV gag and HIV pol proteins.

Purification of stress protein fusions. Two strategies have been developed to purify the recombinant fusion proteins. The T7 system usually produces such large amounts of protein that it forms inclusion bodies, permitting purification by centrifugation. The preliminary results indicate that an hsp70-HIV gag fusion protein accounts for about 20% of total *E. coli* protein in the T7 system. If necessary, other fusion proteins can be purified via the 6-Histidine "tag".

EXAMPLE 3

Adjuvant-Free Carrier Effect of HSP70 IN Vivo

The stress protein fusion vector pKS70 (FIG. 6), containing the T7 RNA polymerase promoter, a polylinker and the *mycobacterial tuberculosis* hsp70 gene, was constructed. The HIV p24 gag gene was subcloned into pKS70 using the Ndel and BamHI sites and the resulting pKS72 vector (FIG. 6) was used to produce the p24-hsp70 fusion protein in *E. coli*. The fusion protein was purified as inclusion bodies and further purified using ATP-agarose chromatography and MonoQ ion exchange chromatography.

The p24-hsp70 protein in phosphate buffered saline (PBS), in the absence of an adjuvant, was injected intraperitoneally into Balb/c mice. As controls, the p24 protein alone in PBS or the hsp70 protein alone in PBS was injected into different groups of mice. Three weeks later, the mice were boosted and finally, three weeks after the boost, the mice were bled. The anti-p24 antibody titer was then determined by ELISA. Mice injected with 25 pmoles of p24-hsp70 had antibody levels 2.7 orders of magnitude higher than mice injected with p24 alone or hsp70 alone (FIG. 7). Results of experiments in which mice were injected with p24 and the adjuvant, alum, also showed that there was an antibody response to p24. In addition, mice injected with the p24-hsp70 fusion protein and mice injected with p24 alone produced a demonstrable T cell response.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A method of inducing or enhancing an immune response in a patient, the method comprising administering to the patient a pharmaceutical composition comprising an isolated fusion protein comprising a stress protein joined via a peptide bond to a heterologous protein or peptide wherein the fusion protein, when administered to the patient, induces or enhances an immune response against the heterologous protein or peptide.

2. The method of claim 1, wherein the stress protein is a mycobacterial stress protein.

3. The method of claim 1, wherein the stress protein is a member of one of the following families of stress proteins: the hsp70 family, the hsp60 family; The groES family; the DnaJ family; the hsp90 family; and the small molecular weight family of stress proteins.

4. The method of claim 1, wherein the stress protein is an *M. bovis* BCG hsp65 protein.

5. The method of claim 1, wherein the fusion protein consists of a stress protein joined via a peptide bond to the hererologous protein or peptide.

6. A method of inducing or enhancing an immune response in a patient, the method comprising administering to the patient a pharmaceutical composition comprising an isolated fusion protein comprising a stress protein joined via a peptide bond to a viral antigen, wherein the fusion protein, when administered to the patient, induces or enhances an immune response against the viral antigen.

7. The method of claim 6, wherein the stress protein is a mycobacterial stress protein.

8. The method of claim 6, wherein the stress protein is a member of one of the following families of stress proteins: the hsp70 family; the hsp60 family; the groES family; The DnaJ family; the hsp90 family; and the small molecular weight family of stress proteins.

9. The method of claim 6, wherein the stress protein is an *M. bovis* BCG hsp65 protein.

10. The method of claim 6, wherein the stress protein is a heat shock protein (hsp) aid the viral antigen is a human immunodeficiency virus (HIV) protein or peptide.

11. The method of claim 10, wherein the HIV protein or peptide is a gag or pol protein or peptide.

12. The method of claim 10, wherein the HIV protein or peptide is a p24 protein or peptide.

13. The method of claim 6, wherein the fusion protein consists of a stress protein joined via a peptide bond to a viral antigen.

14. A method of inducing or enhancing an immune response in a patient, the method comprising administering to the patient a pharmaceutical composition comprising an isolated fusion protein comprising a stress protein joined via a peptide bond to a cancer antigen, wherein the fusion protein, when administered to the patient, induces or enhances an immune response against the cancer antigen.

15. The method of claim 14, wherein the stress protein is a mycobacterial stress protein.

16. The method of claim 14, wherein the stress protein is a member of one of the following families of stress proteins: the hsp70 family; the hsp60 family; the groES family; the DnaJ family; the hsp90 family; and the small molecular weight family of stress proteins.

17. The method of claim 14, wherein the stress protein is an *M. bovis* BCG hsp65 protein.

18. The method of claim 14, wherein the fusion protein consists of a stress protein joined via a peptide bond to a cancer antigen.

19. A method of inducing or enhancing an immune response in a patient, the method comprising administering to the patient a pharmaceutical composition comprising an isolated fusion protein comprising a portion of a stress protein joined via a peptide bond to a heterologous protein or peptide, wherein the fusion protein, when administered to the patient, induces or enhances an immune response against the heterologous protein or peptide.

20. The method of claim 19, wherein the stress protein is a mycobacterial stress protein.

21. The method of claim 19, wherein the stress protein is a member of one of the following families of stress proteins: the hsp70 family; the hsp60 family; the groES family; the DnaJ family; the hsp90 family; and the small molecular weight family of stress proteins.

22. The method of claim 19, wherein the stress protein is an *M. bovis* BCG stress protein.

23. The method of claim 19, wherein the fusion protein consists of a portion of a stress protein joined via a peptide bond to a heterologous protein or peptide.

24. A method of inducing or enhancing an immune response in a patient, the method comprising administering to the patient a pharmaceutical composition comprising an isolated fusion protein comprising a portion of a stress protein joined via a peptide bond to a viral antigen, wherein the fusion protein, when administered to the patient, induces or enhances an immune response against the viral antigen.

25. The method of claim 24, wherein the stress protein is a mycobacterial stress protein.

26. The method of claim 24, wherein the stress protein is a member of one of the following families of stress proteins: the hsp70 family; the hsp60 family; the groES family; the DnaJ family; the hsp90 family; and the small molecular weight family of stress proteins.

27. The method of claim 24, wherein the stress protein is an *M. bovis* BCG hsp65 protein.

28. The method of claim 24, wherein the stress protein is a heat shock protein (hsp) and the viral antigen is a human immunodeficiency virus (HIV) protein or peptide.

29. The method of claim 28, wherein the HIV protein or peptide is a gag or pol protein or peptide.

30. The method of claim 28, wherein the HIV protein or peptide is a p24 protein or peptide.

31. The method of claim 24, wherein the fusion protein consists of a portion of a stress protein joined via a peptide bond to a viral antigen.

32. A method of inducing or enhancing an immune response in a patient, the method comprising administering to the patient a pharmaceutical composition comprising an isolated fusion protein comprising a portion of a stress protein joined via a peptide bond to a cancer antigen, wherein the fusion protein, when administered to the patient, induces or enhances an immune response against the cancer antigen.

33. The method of claim 32, wherein the stress protein is a mycobacterial stress protein.

34. The method of claim 32, wherein the stress protein is a member of one of the following families of stress proteins: the hsp70 family; the hsp60 family; the groES family; the DnaJ family; the hsp90 family; and the small molecular weight family of stress proteins.

35. The method of claim 32, wherein the stress protein is an *M. bovis* BCG hsp65 protein.

36. The method of claim 32, wherein the fusion protein consists of a portion of a stress protein joined via a peptide bond to a cancer antigen.

\* \* \* \* \*

UNITED STATES PATENT AND TRADEMARK OFFICE
CERTIFICATE OF CORRECTION

PATENT NO. : 6,335,183 B1
DATED : January 1, 2002
INVENTOR(S) : Richard A. Young and Douglas Young It is certified that error appears in the above-identified patent and that said Letters Patent is hereby corrected as shown below:

<u>Title page,</u>
Item [75], delete inventor "Douglas Young"

<u>Column 29,</u>
Line 66, replace "aid" with -- and --.

Signed and Sealed this

Second Day of July, 2002

Attest:

Attesting Officer

JAMES E. ROGAN
*Director of the United States Patent and Trademark Office*

(12) EX PARTE REEXAMINATION CERTIFICATE (5677th)
United States Patent
Young

(10) Number: US 6,335,183 C1
(45) Certificate Issued: Feb. 20, 2007

(54) STRESS PROTEINS AND USES THEREFOR

(75) Inventor: Richard A. Young, Weston, MA (US)

(73) Assignee: Whitehead Institute for Biomedical Research, Cambridge, MA (US)

Reexamination Request:
No. 90/006,418, Oct. 22, 2002

Reexamination Certificate for:
Patent No.: 6,335,183
Issued: Jan. 1, 2002
Appl. No.: 08/461,722
Filed: Jun. 5, 1995

Certificate of Correction issued Jul. 2, 2002.

Related U.S. Application Data

(63) Continuation of application No. 08/336,251, filed on Nov. 3, 1994, now abandoned, which is a continuation-in-part of application No. PCT/US94/06362, filed on Jun. 6, 1994, and a continuation-in-part of application No. 08/073,381, filed on Jun. 4, 1993, now abandoned, which is a continuation-in-part of application No. 07/804,632, filed on Dec. 9, 1991, now abandoned, which is a continuation of application No. 07/366,581, filed on Jun. 15, 1989, now abandoned, which is a continuation-in-part of application No. 07/207,298, filed on Jun. 15, 1988, now abandoned, and a continuation-in-part of application No. PCT/US89/02619, filed on Jun. 15, 1989.

(51) Int. Cl.
*C12P 21/04* (2006.01)
*A61K 39/39* (2006.01)
*A61K 39/04* (2006.01)
*C07K 14/00* (2006.01)
*C07K 19/00* (2006.01)

(52) U.S. Cl. .................. 435/69.7; 435/71.1; 424/184.1; 424/188.1; 424/248.1; 530/350

(58) Field of Classification Search ................ 435/69.3, 435/71.1, 320.1, 455, 471, 440, 69.7; 424/184.1, 424/189.1, 192.1, 197.11, 208.1, 209.1, 210.1, 424/248.1, 277.1; 530/350, 402, 403

See application file for complete search history.

(56) References Cited

U.S. PATENT DOCUMENTS

| | | | | |
|---|---|---|---|---|
| 4,666,847 A | * | 5/1987 | Alford et al. | 435/252.33 |
| 4,734,362 A | * | 3/1988 | Hung et al. | 435/68.1 |
| 4,784,941 A | * | 11/1988 | Watanabe et al. | 435/5 |
| 4,797,359 A | * | 1/1989 | Finkelstein | 435/69.1 |
| 4,918,164 A | * | 4/1990 | Hellstrom et al. | 530/387.2 |
| 4,918,166 A | | 4/1990 | Kingsman et al. | |
| 4,963,354 A | * | 10/1990 | Shepard et al. | 424/85.1 |
| 5,204,259 A | * | 4/1993 | Helting et al. | 435/252.3 |
| 5,256,767 A | * | 10/1993 | Salk et al. | 424/208.1 |
| 5,925,362 A | * | 7/1999 | Spitler et al. | 424/277.1 |

FOREIGN PATENT DOCUMENTS

| | | | |
|---|---|---|---|
| EP | 0 118 393 | * | 9/1984 |
| EP | 0 230 222 | * | 9/1987 |
| EP | 0 521 220 | * | 1/1993 |
| WO | WO 90/12030 | * | 9/1990 |

OTHER PUBLICATIONS

Shinnick et al., Infection and Immunity, vol. 56 No. 2, pp. 446–451 (Feb. 1988).*
Shinnick et al., Infection and Immunity, vol. 55 No. 8, pp. 1932–1935 (Aug. 1987).*
Jacobs et al., Nature, vol. 327 No. 6122, pp. 532–535 (Jun. 1987).*
Snapper et al., Proceedings of the National Academy of Sciences, USA, vol. 85 No. 18, pp. 6987–6991 (Sep. 1988).*
NCBI Accession NP_854111, 60 KDA Chaperonin, Apr. 2005.*
Britton et al., Leprosy Review, vol. 57 Supp 2, pp. 67–75 (1986).*
Farrelly et al., Journal of Biological Chemistry, vol. 259 No. 9, pp. 5745–5751 (May 1984).*
Bardwell et al., Journal of Biological Chemistry, vol. 261 No. 4, pp. 1782–1785 (Feb. 1986).*
Chandrasekhar et al., Journal of Biological Chemistry, vol. 261 No. 26, pp. 12414–12419 (Sep. 1986).*
Lindquist, Annual Review of Biochemistry, vol. 55, pp. 1151–1191 (Jul. 1986).*
Garsia et al., Infection and Immunity, vol. 57 No. 1, pp. 204–212 (Jan. 1989).*
Salgaller et al., Cancer Research, vol. 53 No. 9, pp. 2154–2161 (May 1993).*
Sakai et al., Journal of Biological Chemistry, vol. 260 No. 5, pp. 5055–5060 (Apr. 1985).*
Tao et al., Nature, vol. 362 No. 6422, pp. 755–758 (Apr. 1993).*
NCBI Accession CAD93221, Probable Chaperone protein DNAK . . . , Apr. 2005.*
Spindler et al., Journal of Virology, vol. 49 No. 1, pp. 132–141 (Jan. 1984).*
Aldovini et al., Nature, vol. 351 No. 6326, pp. 479–482 (Jun. 1991).*
Davis et al., Gene, vol. 21 No. 3, pp. 273–274 (Mar. 1983).*
Giudice et al., Research in Immunology, vol. 142 No. 8, pp. 703–707 (Oct. 1991).*
Gomez et al., Infection and Immunity, vol. 60 No. 7, pp. 2565–2571 (Jul. 1992).*

(Continued)

*Primary Examiner*—James C. Housel

(57) ABSTRACT

The present invention relates to stress proteins and methods of modulating an individual's immune response. In particular, it relates to the use of such stress proteins in immune therapy and prophylaxis, which results in an induction or enhancement of an individual's immune response and as an immunotherapeutic agent which results in a decrease of an individual's immune response to his or her own cells. The present invention also relates to compositions comprising a stress protein joined to another component, such as a fusion protein in which a stress protein is fused to an antigen. Further, the present invention relates to a method of generating antibodies to a substance using a conjugate comprised of a stress protein joined to the substance.

OTHER PUBLICATIONS

Anthony et al., Abstract S16 in the Final Program and Abstracts Book for The Fifth Annual Conference on Vaccine Research, held May 6–8, 2002.

Brewer et al., "Engineering Proteins to Enable Their Isolation in a Biologically Active Form" in *Purification and Analysis of Recombinant Proteins,* Seltharam and Sharma (Eds.), Marcel Dekker, Inc., NY (1991).

Chu et al., *Clin. Exp. Immunol.* 121:216–225 (2000).

Delmas et al., *Bioconjugate Chem.* 3:80–84 (1992).

Derkay et al., Abstract 633 on p. 443 of the Final Program for the 21st International Papillomavirus Conference & Clinical Workshop (2004).

Dintzis, *Pediatric Research* 32:376–385 (1992).

Einstein et al., Abstract 8 in the Abstract Book and Final Program for The Annual Meeting on Women's Cancer™; The Society of Gynecologic Oncologists' 36th Annual Meeting, Mar. 19–23, 2005.

Flaherty et al., *Nature* 346:623–628 (1990).

Goldstone et al., *Dis. Colon Rectum* 45:502–507 (2002).

Gupta et al., *Vaccine* 11:293–306 (1993).

Hearn and Acosta, *J. Mol. Recognition* 14:323–369 (2001).

Hedstrom et al., *J. Exp. Med.* 165:1430–1435 (1987).

Huang et al., *J. Exp. Med.* 191:403–408 (2000).

Liu et al., Abstract Th25.22 in *Clin. Invest. Med.,* vol. 27, p. 73D (2004).

Palliser et al., *J. Immunol.* 174:1879–1887 (2005).

Pedersen et al., *Protein Expression and Purification* 15:389–400 (1999).

Raychaudhuri and Morrow, *Immunology Today* 14:344–348 (1993).

Klinkert, M., et al., "Surface Proteins of *Mycoplasma hyopneumoniae* Identified from an *Escherichia coli* Expression Plasmid Library," *Infection and Immunity* 49(2):329–335 (1985).

Rambukkana, A., et al., "Identification and Characterization of Epitopes Shared between the Mycobacterial 65–Kilodalton Heat Shock Protein and the Actively Secreted Antigen 85 Complex: Their In Situ Expression on the Cell Wall Surface of *Mycobacterium leprae,*" *Infection and Immunity* 60(11):4517–4527 (1992).

Thole, J., et al., "Characterization, Sequence Determination, and Immunogenicity of a 64–Kilodalton Protein of *Mycobacterium bovis* BCG Expressed in *Escherichia coli* K–12," *Infection and Immunity* 55(6): 1466–1475 (1987).

Thole, J., et al., "Use of Recombinant Antigens Expressed in *Escherichia coli* K–12 TO Map B–Cell and T–Cell Epitopes on the Immunodominant 65–Kilodalton Protein of *Mycobacterium bovis* BCG," *Infection and Immunity* 56(6): 1633–1640 (1988).

Wang, T., et al., "Identification of the Peptide Biding Domain of hsc70," *J. Biol. Chem.,* 268(35):26049–26051 (1993).

Agterberg, M., et al., "Outer Membrane PhoE Protein of *Escherichia coli* as a Carrier for Foreign Antigenic Determinants: Immunogenicity of Epitopes of Foot–and–Mouth Disease Virus," *Vaccine* 8:85–91 (Feb. 1990).

Agterberg, M., et al., "Outer Membrane Protein PhoE as a Carrier for the Exposure of Foreign Antigenic Determinants at the Bacterial Cell Surface," *Antonie van Leeuwenhock* 59:249–262 (1991).

Agterberg, M., et al., "Protection of Guinea–pigs Against Foot–and–Mouth Disease Virus by Immunization with a PhoE FMDV Hybrid Protein," *Vaccine* 8:438–440 (Oct. 1990).

Allen, P.M., et al., "T–Cell Recognition of Lysozyme: The Biochemical Basis of Presentation," *Immunological Reviews* 98:171–187 (1987).

Amory Siosson, L.M., et al., "Induction of Protective Immunity in Mice Using A 62–kDa Recombinant Fragment of a *Schistosoma mansoni* Surface Antigen," *J. of Immunol.,* 149(11):3612–3620 (1992).

Bayliss, C.D., et al., "A Recombinant Fowlpox Virus That Expresses the VP2 Antigen of Infectious Bursal Disease Virus Induces Protection Against Mortality Caused by the Virus," *Arch Virol.* 120:193–205 (1991).

Billman–Jacobe, H., et al., "Mapping of the T and B Cell Epitopes of the *Mycobacterium bovis* Protein, MPB70," *Immunol. Cell Biol.* 68:359–365 (1990).

Blachere, N.E., et al., "Heat Shock Protein Vaccines Against Cancer," *J. Immunotherapy* 14(4):352–356 (1993).

Brett, S.J., et al., "Influences of Antigen Processing on the Expression of the T Cell Repertoire," *J. Exp. Med.* 168:357–373 (Jul. 1988).

Burrows, P.D., et al., "B–Cell Development in Man," *Curr. Opinion Biol.* 5:201–206 (1993).

Cane, P.A., et al., "Reduction of Yellow Fever Virus Mouse Neurovirulence by Immunization with a Bacterially Synthesized Non–structural Protein (NS1) Fragment," *J. Gen. Virol.* 69:1241–1246 (1988).

Chong, P., et al., "Identification of a Potent Synthetic HIV1 Immunogen Comprising gag–P24 Tandem T– and B–Cell Epitopes," *FEBS* 264(2):231–234 (May 1990).

Ciborowski, P., et al., "Immunological response to a *Staphylococcus aureus* fibronectin–binding protein," *J. Med. Microbiol.,* 37:376–381 (1992).

Clarke, B.E., et al., "Improved Immunogenicity of a Peptide Epitope After Fusion to Hepatitis B Core Protein," *Nature* 330:381–384 (Nov. 1987).

Clarke, B.E., et al., "Presentation and immunogenicity of viral epitopes on the surface of hybrid hepatitis B virus core particles produced in bacteria," *J. of General Virology,* 71:1109–1117 (1990).

Clough, E.R., et al., "Production of Anti–Sporozoite Antibodies in Absence of Response to Carrier By Coupling an MDP Derivative to a Malaria Peptide–Tetanus Toxoid Conjugate," *Biochemical and Biophysical Research Communications,* 131(1):70–75 (1985).

Crane, M.S., et al., "Cross–Protection Against Four Species of Chicken Coccidia with a Single Recombinant Antigen," *Infection and Immunity* 59(4):1271–1277 (Apr. 1991).

Decision Revoking European Patent EP–B–0419569.

European Patent No. 0700445 B1; Opposition By Antigenics, Inc.: Statement of Grounds of Opposition.

Drew, M.D., et al., "Vaccination By Cholera Toxin Conjugated to a Herpes Simplex Virus Type 2 Glycoprotein D Peptide," *J. General Virol.* 73:2357–2366 (1992).

Emmrich, F., et al., "A Recombinant 64 Kilodalton Protein of *Mycobacterium bovis* Bacillus Calmette–Guerin Specifically Stimulates Human T4 Clones Reactive to Mycobacterial Antigens," *J. Exp. Med.* 163:1024–1029 (Apr. 1986).

Etlinger, H.M., et al., "Antibody Responses to a Synthetic Peptide–Based Malaria Vaccine Candidate: Influence of Sequence Variants of the Peptide," *Eur. J. Immunol.* 21:1505–1511 (1991).

Finnegan, A., et al., "The T Cell Repertoire For Recognition of a Phylogenetically Distant Protein Antigen—Peptide Specificity and MHC Restriction of Staphylococcal Nuclease–specific T Cell Clones," *J. Exp. Med.* 164:897–910 (Sep. 1986).

Francis, M.J., et al., "Non–Responsiveness to a Foot–and–Mouth Disease Virus Peptide Overcome by Addition of Foreign Helper T–Cell Determinants," *Nature* 330:168–170 (Nov. 1987).

Freimuth, P., et al., "Insertion of Myoglobin T–Cell Epitopes Into the *Escherichia coli* Alkaline Phosphatase," *Res. Microbiol.* 141:995–1001 (1990).

Fuqua, S.A.W., et al., "Induction of the Estrogen–regulated "24K" Protein by Heat Shock," *Cancer Research* 49:4126–4129 (Aug. 1, 1989).

Gammon, G., et al., "The Choice of T–Cell Epitopes Utilized on a Protein Antigen Depends on Multiple Factors Distant from, as well as at the Determinant Site," *Immunological Reviews* 98:53–73 (1987).

Good, M.F., et al., "Construction of Synthetic Immunogen: Use of New T–Helper Epitope on Malaria Circumsporozoite Protein," *Science* 235:1059–1062 (Feb. 1987).

Handman, E., et al., "*Leishmania major:* Production of Recombinant gp63, Its Antigenicity and Immunogenicity in Mice," *Experimental Parasitology* 70:427–435 (1990).

Hinuma, S., et al., "A Novel Strategy For Converting Recombinant Viral Protein Into High Immunogenic Antigen," *FEBS* 288(1,2):138–142 (Aug. 1991).

Hogervorst, E.M., et al., "Efficient Recognition by Rat T Cell Clones of an Epitope of Mycobacterial hsp 65 Inserted in *Escherichia coli* Outer Membrane Protein PhoE," *Eur. J. Immunol.* 20:2763–2768 (1990).

Janvier, B., et al., "Immune Response to a Major Epitope of p24 During Infection with Human Immunodeficiency Virus Type 1 and Implications for Diagnosis and Prognosis," *J. Clinical Microbiol.* 29(3):488–492 (Mar. 1991).

Jarrett, W.F.H., et al., "Studies on Vaccination against Papillomaviruses: Prophylactic and Therapeutic Vaccination with Recombinant Structural Proteins," *Virology,* 184:33–42 (1991).

Jin, X.W., et al., "Bovine Serological Response to a Recombinanty BPV–1 Major Caspid Protein Vaccine," *Intervirology* 31:345–354 (1990).

Johnston, J.M., et al., "Antigenic and Immunogenic Properties of a Hepatitis A Virus Capsid Protein Expressed in *Escherichia coli,*" *J. Infect. Diseases* 157(6):1203–1211 (Jun. 1988).

Kazura, J.W., et al., "Protective Efficacy of a Cloned *Brugia malayi* Antigen in a Mouse Model of Microfilaremia," *J. Immunol.* 145(7):2260–2264 (Oct. 1990).

Kit, M., et al., "Bovine Herpesvirus–1 (Infectious Bovine Rhinotracheitis Virus)–Based Viral Vector Which Expresses Foot–and–Mouth Disease Epitopes," *Vaccine* 9: 564–572 (Aug. 1991).

Knapp, B., et al., "A Histidin Alanine Rich Recombinant Antigen Protects Aotus Monkeys from *P. Falciparium* Infection," *Behring Inst. Mitt.* 82:349–359 (1988).

Krzych, U., et al., "Repertoires of T Cells Directed Against A Large Protein Antigen, β–Galactosidase," *J. Immunol.* 128(4):1529–1534 (Apr. 1982).

Lamb, J.R., et al., "Mapping of T Cell Epitopes Using Recombinant Antigens and Synthetic Peptides," *The EMBO J.* 6(5):1245–1249 (1987).

Lamb, F.I., et al., "Heterologous Expression of the 65–Kilodalton Antigen of *Mycobacterium leprae* and Murine T–Cell Responses to the Gene Product," *Infection and Immunity* 56(5):1237–1241 (May 1988).

Lawrence, R.M., et al., "Expression of the Cloned Gene for Enterotoxin Stb of *Escherichia coli,*" *Infection and Immunity,* 58(4):970–977 (1990).

Leclerc, C., et al., "A Synthetic Vaccine Constructed by Copolymerization of B and T Cell Determinants," *Eur. J. Immunol.* 17:269–273 (1987).

Lee, A.C.J., et al., "A Method for Preparing β–hCG Cooh Peptide–Carrier Conjugates of Predictable Composition," *Molecular Immunology,* 17:749–756 (1980).

Lehner, T., et al., "Identification of T– and B–CellEpitopes in Synthetic Peptides Derived From a *Streptococcus Mutans* Protein and Characterization of Their Antigenicity and Immunogenicity," *Archs oral Biol.* 35, Suppl:39S–45S (1990).

Linsley, P.S., et al., "T–Cell Antigen CD28 Mediates Adhesion With B Cells By Interacting With Activation Antigen B7/BB–1," *Proc. Natl. Acad. Sci. USA* 87:5031–5035 (Jul. 1990).

Löwenadler, B., et al., "T and B Cell Responses To Chimeric Proteins Containing Heterologous T Helper Epitopes Inserted At Different Positions," *Molecular Immunology* 29(10):1185–1190 (1992).

Löwenadler, B., et al., "Enhanced Immunogenicity of Recombinant Peptide Fusions Containing Multiple Copies of a Heterologous T Helper Epitope," *Eur. Immunol.* 20:1541–1545 (1990).

Löwenadler, B., et al., "A recombinant *Escherichia coli* heat–stable enterotoxin (Sta) fusion protein eliciting anti–STa neutralizing antibodies," *FEMS Microbiology Letters,* 82:271–277 (1991).

McKenzie, K.R., et al., "Sequence and Immunogenicity of the 70–kDa Heat Shock Protein of *Mycobacterium leprae,*" *J. Immunol.* 147(1):312–319 (Jul. 1991).

Mehra, V., et al., "Efficient Mapping of Protein Antigenic Determinants," *Proc. Natl. Acad. Sci. USA* 83:7013–7017 (Sep. 1986).

Merrick, R.M., et al., "The Use of β–Galactosidase Fusion Proteins Encoding the Early Region 1 Transforming Proteins of Adenovirus Type 12 to Examine the Humoral Response in Tumor–Bearing Animals," *J. Gen. Virol.* 72:955–960 (1991).

Miller, G.A., et al., "Characterization and Vaccine Potential of a Novel Recombinant Coccidial Antigen," *Infection and Immunity,* 57(7):2014–2020 (1989).

Moore, S.K., et al., "Murine 86– and 84–kDa Heat Shock Proteins, cDNA Sequences, Chromosome Assignments, and Evolutionary Origins," *J. Biol. Chem.* 264(10):5343–5351 (1989).

Morgan, D.O., et al., "Protection of Cattle and Swine Against Foot–and–Mouth Disease, Using Biosynthetic Peptide Vaccines," *Am. J. Vet. Res.* 51(1):40–45 (Jan. 1990).

Morimoto, R.I., "Cells in Stress: Transcriptional Activation of Heat Shock Genes," *Science* 259:1409–1410 (Mar. 1993).

Moser, D., et al., "The Humoral Response to Heat Shock Protein 70 in Human and Murine *Schistosomiases mansoni,*" *Parasite Immunol.* 12:341–352 (1990).

Oberg, L.A., et al., "Bacterially Expressed Nucleoprotein of Infectious Hematopoietic Necrosis Virus Augments Protective Immunity Induced by the Glycoprotein Vaccine in Fish," *J. Virol.* 65:4486–4489 (Aug. 1991).

Oftung, F., et al., "Human T Cell Clones Recognize Two Abundant *Mycobacterium tuberculosis* Protein Antigens Expressed in *Escherichia coli*," *J. Immunol.* 138(3):927–931 (Feb. 1987).

Owens, T., et al., "The Cell Biology of T–dependent B Cell Activation," Leucocytes: Functions and Pathogenesis, *Biochem. Cell Biol.* 67:481–489 (1989).

Partidos, C.D., et al., "Immune Responses in Mice Following Immunization With Chimeric Synthetic Peptides Representing B and T Cell Epitopes of Measles Virus Proteins," *J. Gen. Virol.* 72:1293–1299 (1991).

Peeters, J.M., et al., "Comparison of four bifunctional reagents for coupling peptides to proteins and the effect of the three moieties on the immunogenicity of the conjugates," *J. of Immunol. Methods,* 120:133–143 (1989).

Phalipon, A., et al., "Expression of a poliovirus type 1 neutralization epitope on a diphtheria toxin fusion protein," *Vaccine,* 7:132–136 (1989).

Rand, K.N., et al., "Cloning and Expression of a Protective Antigen from the Cattle Tick *Boophilus microplus*," *Proc. Natl. Acad. Sci. USA* 86:9657–9661 (Dec. 1989).

Rickard, M.D., "Cestode Vaccines," *Southeast Asian J. Trop. Med.. Public Health,* 22: 287–290.

Rossi–Campos, A., et al., "Immunization of pigs against *Actinobacillus pleuropneumoniae* with two recombinant protein preparations," *Vaccine,* 10(8):512–518 (1992).

Rothbard, J.B., et al., "A Sequence Pattern Common to T Cell Epitopes," *The EMBO J.* 7(1):93–100 (1988).

Sad, S., et al., "Bypass of Carrier–Induced Epitope–Specific Suppression Using a T–Helper Epitope," *Immunology* 76:599–603 (1992).

Schödel, F., et al., "Synthesis in *Vibrio cholerae* and Secretion of Hepatitis B Virus Antigens Fused to *Escherichia coli* Heat–Labile Entertoxin Subunit B," *Gene* 99:255–259 (1991).

Smith, D.B., et al., "$M_r$ 26,000 antigen of *Schistosoma japonicum* recognized by resistant WEHI 129/J mice is a parasite glutathione S–transferase," *Proc. Natl. Acad. Sci. USA* 83:8703–8707 (1986).

Spindler, K.R., et al., "Analysis of Adenovirus Transforming Proteins from Early Regions 1A and 1B with Antisera to Inducible Fusion Antigens Produced in *Escherichia coli*,"*J. Virol.* 49(1):132–141 (Jan. 1984).

Ståhl, S., et al., "A Dual Expression System for the Generation, Analysis and Purification of Antibodies to a Repeated Sequence of the *Plasmodium falciparum* Antigen Pf155/RESA," *J. Immunological Methods* 124:43–52 (1989).

Su, G., et al., "Extracellular export of Shiga toxin B–subunit/ haemolysin A (C–terminus) fusion protein expressed in *Salmonella typhimurium aroA*–mutant and stimulation of B–subunit specific antibody responses in mice," *Microbial Pathogenesis,* 13:465–476 (1992).

Suzue, K., et al., "Heat Shock Proteins as Immunological Carriers and Vaccines," *Stress–Inducible Cellular Responses* (U. Feige, R. I. Morimoto, I. Yahara, B. S. Polla, eds.), Birkhauser/Springer, 77: 451–465 (1996).

Talwar, G.P., et al., "Enhancement of antigonadotropin response to the β–subunit of ovine luteinizing hormone by carrier conjugation and combination with the β–subunit of human chorionic gonadotropin," *Fertility and Sterility,* 46(1):120–126 (1986).

Tetzlaff, C.L., et al., "Induction of Proliferative Responses of T Cells from *Babesia bovis*–Immune Cattle with a Recombinant 77–Kilodalton Merozoite Protein (Bb–1)," *Infection and Immunity,* 60(2):644–652 (1992).

Thanavala, Y.M., et al., "Affinity, cross–reactivity and biological effectiveness of rabbit antibodies against a synthetic 37 amino acid C–terminal peptide of human chorionic gonadotrophin," *Clin. Exp. Immunol.,* 39:112–118 (1980).

Thole, J.E.R., et al., "Use of Recombinant Antigens Expressed in *Escherichia coli* K–12 To Map B–Cell and T–Cell Epitopes on the Immunodominant 65–Kilodalton Protein of *Mycobacterium bovis* BCG," *Infection and Immunity* 56(6):1633–1640 (Jun. 1988).

Tommassen, J., et al., "Molecular Analysis of the Promoter Region of the *Escherichia coli* K–12 *phoE* Gene—Identification of an Element, Upstream from the Promoter, Required for Efficient Expression of PhoE Protein," *Mol. Biol.* 198:633–641 (1987).

Udono, H., et al., "Comparison of Tumor–Specific Immunogenicities of Stress–Induced Proteins gp96, hsp90, and hsp70," *J. Immunol. 152*: 5398–5403 (Jun. 1994).

Ullrich, S.J., et al., "Transcriptional and Translational Analysis of the Murine 84– and 86–kDa Heat Shock Proteins," *J. Biol. Chem.* 264(12):6810–6816 (1989).

Vreden, S.G.S., et al., "Phase I Clinical Trial of a Recombinant Malaria Vaccine Consisting of the Circumsporozoite Repeat Region of *Plasmodium Falciparum* Coupled to Hepatitis B Surface Antigen," *Am. J. Trop. Med. Hyg.,* 45(5):533–538 (1991).

Xu, L., et al., "Epitope Mapping and Characterization of the Infectious Hematopoietic Necrosis Virus Glycoprotein, Using Fusion Proteins Synthesized in *Escherichia coli*,", *J. Virol.* 65(3):1611–1615 (Mar. 1991).

Zavala, F., et al., "Synthetic Peptide Vaccine Confers Protection Against Murine Malaria," *J. Exp. Med.,* 166:1591–1596 (1987).

November 2000 Printout of a Web Page of Stressgen Biotechnologies (http//stressgen.com).

Barrios et al., 1992, "Mycobacterial heat–shock proteins as carrier molecules. II. The use of the 70–kDa mycobacterial heat–shock protein as carrier for conjugated vaccines can circumvent the need for adjuvants and Bacillus Calmette Guérin priming", Eur. J. Immunol. 22:1365–1372.

Brett et al., 1989, "Differential pattern of T cell recognition of the 65–kDa mycobacterial antigen following immunization with the whole protein or peptides", Eur. J. Immunol. 19:1303–1310.

Cox et al., 1988, "Orientation of epitopes influences the immunogenicity of synthetic peptide dimers", Eur. J. Immunol. 18:2015–2019.

Engel et al., 1991, "Generation of antibodies against human hsp27 and murine hsp25 by immunization with a chimeric small heat shock protein", Biomed. Biochim. Acta 50:1065–1071.

Francis et al., 1989, "Peptide vaccines based on enhanced immunogenicity of peptide epitopes presented with T–cell determinants or hepatitis B core protein", Meth. Enzymol. 178:659–676.

Fyfe et al., 1991, "Murine immune response to HIV–1 p24 core protein following subcutaneous, intraperitoneal and intravenous immunization", Immunology 74:467–472.

Lussow et al., 1991, "Mycobacterial heat–shock proteins as carrier molecules", Eur. J. Immunol. 21:2297–2302.

Myers, 1991, "Role of B cell antigen processing and presentation in the humoral immune response", FASEB J. 5:2547–2553.

Parker, 1993, "T-cell dependent B cell activation", Annu. Rev. Immunol. 11:331–360.

Thole et al., 1987, "Characterization, sequence determination, and immunogenicity of a 64-kilodalton protein of *Mycobacterium bovis* BCG expressed in *Escherichia coli* K–12", Infect. Immun. 55:1466–1475.

Townsend et al., 1989, "Antigen recognition by class I–restricted T lymphocytes", Ann. Rev. Immunol. 7:601–624.

van Eden et al., 1988, "Cloning of the mycobacterial epitope recognized by T lymphocytes in adjuvant arthritis", Nature 331:171–173.

Yewdell et al., 1990, "The binary logic of antigen processing and presentation to T cells", Cell 62:203–206.

Young et al., 1988, "Stress proteins are immune targets in leprosy and tuberculosis", Proc. Natl. Acad. Sci. USA 85:4267–4270.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–18 is confirmed.

Claim 33 is cancelled.

Claims 19, 24 and 32 are determined to be patentable as amended.

Claims 20–23, 25–31 and 34–36, dependent on an amended claim, are determined to be patentable.

New claims 37–98 are added and determined to be patentable.

19. A method of inducing or enhancing an immune response in a *human* patient, the method comprising administering to the *human* patient a pharmaceutical composition comprising an isolated fusion protein comprising a portion of a stress protein joined via a peptide bond to a heterologous protein or peptide, wherein the fusion protein, when administered to the *human* patient, induces or enhances an immune response against the heterologous protein or peptide, *and wherein the amino acid sequence of the portion of the stress protein is identical to at least 40% of the sequence of the stress protein.*

24. A method of inducing or enhancing an immune response in a *human* patient, the method comprising administering to the *human* patient a pharmaceutical composition comprising an isolated fusion protein comprising a portion of a stress protein joined via a peptide bond to a viral antigen, wherein the fusion protein, when administered to the *human* patient, induces or enhances an immune response against the viral antigen, *and wherein the amino acid sequence of the portion of the stress protein is identical to at least 40% of the sequence of the stress protein.*

32. A method of inducing or enhancing an immune response in a *human* patient, the method comprising administering to the *human* patient a pharmaceutical composition comprising an isolated fusion protein comprising a portion of a stress protein joined via a peptide bond to a cancer antigen, wherein the fusion protein, when administered to the *human* patient, induces or enhances an immune response against the cancer antigen, *and wherein the amino acid sequence of the portion of the stress protein is identical to at least 40% of the sequence of the stress protein.*

*37. The method of claim 1, wherein the patient is a human patient.*

*38. The method of claim 6, wherein the patient is a human patient.*

*39. The method of claim 14, wherein the patient is a human patient.*

*40. A method of inducing or enhancing an immune response in a patient in need thereof, the method comprising administering to the patient a pharmaceutical composition comprising an isolated fusion protein comprising a portion of a stress protein of the hsp70 family, the groES family, the DnaJ family, or the hsp90 family, joined via a peptide bond to a heterologous protein or peptide, wherein the fusion protein, when administered to the patient, induces or enhances an immune response against the heterologous protein or peptide, and wherein the amino acid sequence of the portion of the stress protein is identical to at least 40% of the sequence of the stress protein.*

*41. The method of claim 40, wherein the stress protein is a mycobacterial stress protein.*

*42. The method of claim 41, wherein the mycobacterial stress protein is an M. bovis BCG stress protein.*

*43. The method of claim 40, wherein the patient is a human patient.*

*44. The method of claim 40, wherein the pharmaceutical composition consists of the fusion protein and a pharmaceutically acceptable carrier or excipient.*

*45. The method of claim 40, wherein the heterologous protein or peptide is a viral antigen.*

*46. The method of claim 40, wherein the heterologous protein or peptide is a cancer antigen.*

*47. The method of claim 40, wherein the heterologous protein or peptide is an HIV protein or peptide or an influenza virus hemagglutinin protein.*

*48. The method of claim 40, wherein the heterologous protein or peptide is a CEA, AFP, or PSA antigen.*

*49. The method of claim 40, wherein the pharmaceutical composition is free of added adjuvant.*

*50. A method of inducing or enhancing an immune response in a patient in need thereof, the method comprising administering to the patient a pharmaceutical composition comprising an isolated fusion protein comprising a portion of a stress protein of the hsp70 family, the groES family, the DnaJ family, the hsp90 family, or the small molecular weight hsp family, joined via a peptide bond to a viral antigen, wherein the fusion protein, when administered to the patient, induces or enhances an immune response against the viral antigen, and wherein the amino acid sequence of the portion of the stress protein is identical to at least 40% of the sequence of the stress protein.*

*51. The method of claim 50, wherein the stress protein is a mycobacterial stress protein.*

*52. The method of claim 51, wherein the mycobacterial stress protein is an M. bovis BCG stress protein.*

*53. The method of claim 52, wherein the M. bovis BCG stress protein is an M. bovis BCG hsp70 stress protein.*

*54. The method of claim 50, wherein the patient is a human patient.*

55. The method of claim 50, wherein the pharmaceutical composition consists of the fusion protein and a pharmaceutically acceptable carrier or excipient.

56. The method of claim 50, wherein the fusion protein consists of the portion of a stress protein joined via a peptide bond to the viral antigen.

57. The method of claim 50, wherein the viral antigen is an HIV protein or peptide or an influenza virus hemagglutinin protein.

58. The method of claim 50, wherein the pharmaceutical composition is free of added adjuvant.

59. A method of inducing or enhancing an immune response in a patient, the method comprising administering to the patient a pharmaceutical composition comprising an isolated fusion protein comprising a portion of a stress protein of the hsp60 family, the hsp70 family, the groES family, the DnaJ family, or the hsp90 family, joined via a peptide bond to a cancer antigen, wherein the fusion protein, when administered to the patient, induces or enhances an immune response against the cancer antigen, and wherein the amino acid sequence of the portion of the stress protein is identical to at least 40% of the sequence of the stress protein.

60. The method of claim 59, wherein the stress protein is a mycobacterial stress protein.

61. The method of claim 60, wherein the mycobacterial stress protein is an M. bovis BCG stress protein.

62. The method of claim 61, wherein the M. bovis BCG stress protein is an M. bovis BCG hsp65 stress protein.

63. The method of claim 59, wherein the patient is a human patient.

64. The method of claim 59, wherein the pharmaceutical composition consists of the fusion protein and a pharmaceutically acceptable carrier or excipient.

65. The method of claim 59, wherein the fusion protein consists of the portion of a stress protein joined via a peptide bond to the cancer antigen.

66. The method of claim 59, wherein the cancer antigen is a CEA, AFP, or PSA antigen.

67. The method of claim 59, wherein the pharmaceutical composition is free of added adjuvant.

68. A method of inducing or enhancing an immune response in a patient, the method comprising administering to the patient a pharmaceutical composition comprising an isolated fusion protein comprising a portion of a mycobacterial stress protein joined via a peptide bond to a cancer antigen, wherein the fusion protein, when administered to the patient, induces or enhances an immune response against the cancer antigen, and wherein the amino acid sequence of the portion of the mycobacterial stress protein is identical to at least 40% of the sequence of the stress protein.

69. The method of claim 68, wherein the mycobacterial stress protein is an M. bovis BCG stress protein.

70. The method of claim 69, wherein the M. bovis BCG stress protein is an M. bovis BCG hsp65 stress protein.

71. The method of claim 68, wherein the patient is a human patient.

72. The method of claim 68, wherein the pharmaceutical composition consists of the fusion protein and a pharmaceutically acceptable carrier or excipient.

73. The method of claim 68, wherein the fusion protein consists of the portion of a mycobacterial stress protein joined via a peptide bond to the cancer antigen.

74. The method of claim 68, wherein the cancer antigen is a CEA, AFP, or PSA antigen.

75. The method of claim 68, wherein the pharmaceutical composition is free of added adjuvant.

76. A method of inducing or enhancing an immune response in a patient, the method comprising administering to the patient a pharmaceutical composition comprising an isolated fusion protein consisting of a portion of a stress protein joined via a peptide bond to a viral antigen, wherein the fusion protein, when administered to the patient, induces or enhances an immune response against the viral antigen.

77. The method of claim 76, wherein the stress protein is an hsp.

78. The method of claim 76, wherein the stress protein is a member of one of the following families of stress proteins: the hsp70 family; the hsp60 family; the groES family; the DnaJ family; the hsp90 family; and the small molecular weight family of stress proteins.

79. The method of claim 76, wherein the stress protein is a mycobacterial stress protein.

80. The method of claim 79, wherein the mycobacterial stress protein is an M. bovis BCG stress protein.

81. The method of claim 80, wherein the M. bovis BCG stress protein is an M. bovis BCG hsp65 stress protein.

82. The method of claim 76, wherein the viral antigen is an HIV protein or peptide or an influenza virus hemagglutinin protein.

83. The method of claim 76, wherein the pharmaceutical composition consists of the fusion protein and a pharmaceutically acceptable carrier or excipient.

84. The method of claim 76, wherein the pharmaceutical composition is free of added adjuvant.

85. The method of claim 76, wherein the patient is a human patient.

86. The method of claim 81, wherein the patient is a human patient.

87. The method of claim 1, wherein the pharmaceutical composition is free of added adjuvant.

88. The method of claim 6, wherein the viral antigen is an influenza virus hemagglutinin protein.

89. The method of claim 2, wherein the patient is a human patient.

90. The method of claim 14, wherein the cancer antigen is a CEA, AFP, or PSA antigen.

91. The method of claim 4, wherein the patient is a human patient.

92. The method of claim 19, wherein the pharmaceutical composition is free of added adjuvant.

93. The method of claim 24, wherein the viral antigen is an influenza virus hemagglutinin protein.

94. The method of claim 15, wherein the patient is a human patient.

95. The method of claim 32, wherein the cancer antigen is a CEA, AFP, or PSA antigen.

96. The method of claim 17, wherein the patient is a human patient.

97. The method of claim 50, wherein the viral antigen is an antigen of a virus that is pathogenic in the patient.

98. The method of claim 40, wherein the pharmaceutical composition is suitable for administration to a human.

* * * * *